US006512161B1

(12) United States Patent
Rouy et al.

(10) Patent No.: US 6,512,161 B1
(45) Date of Patent: Jan. 28, 2003

(54) TRANSGENIC RABBIT THAT EXPRESSES A FUNCTIONAL HUMAN LIPOPROTEIN (A)

(75) Inventors: Didier Rouy, Thiais (FR); Nicolas Duverger, Paris (FR); Florence Emmanuel, Aubervilliers (FR); Patrice Denefle, Saint Maur (FR); Louis-Marie Houdebine, Buc (FR); Celine Viglietta, Versailles (FR); Edward M. Rubin, Berkeley, CA (US); Steven D. Hughes, Oakland, CA (US)

(73) Assignee: Aventis Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 09/227,701

(22) Filed: Jan. 8, 1999

Related U.S. Application Data
(60) Provisional application No. 60/070,727, filed on Jan. 8, 1998.

(51) Int. Cl.[7] .................. G01N 33/00; A01K 67/00; A01K 67/027; C12N 15/00
(52) U.S. Cl. ................. 800/3; 800/14; 800/9; 800/13; 800/22; 800/23; 800/24; 800/25
(58) Field of Search .................. 800/3, 9, 13, 14, 800/22, 23, 24, 25; 435/440, 455

(56) References Cited

U.S. PATENT DOCUMENTS

| | | | |
|---|---|---|---|
| 4,797,368 A | 1/1989 | Carter et al. ............... 435/320 |
| 4,861,719 A | 8/1989 | Miller ....................... 435/236 |
| 5,139,941 A | 8/1992 | Muzyczka et al. ....... 435/172.3 |
| 5,168,062 A | 12/1992 | Stinski ................... 435/240.2 |
| 5,385,839 A | 1/1995 | Stinski ................... 435/240.2 |
| 5,434,058 A | 7/1995 | Davidson ................. 435/69.1 |
| 5,580,859 A | 12/1996 | Felgner et al. .............. 514/44 |
| 5,589,466 A | 12/1996 | Felgner et al. .............. 514/44 |
| 5,792,902 A | * 8/1998 | Benoit et al. ................ 800/2 |
| 5,877,399 A | * 3/1999 | Hsiao et al. ................. 800/2 |

FOREIGN PATENT DOCUMENTS

| | | |
|---|---|---|
| AU | B-67878/94 | 12/1994 |
| EP | 0 178 220 | 1/1992 |
| EP | 0 140 308 | 1/1993 |
| EP | 0 488 528 | 11/1995 |
| EP | 0 453 242 | 8/1996 |
| WO | WO 89/07150 | 8/1989 |
| WO | WO 90/02806 | 3/1990 |
| WO | WO 91/18088 | 11/1991 |
| WO | WO 93/09239 | 5/1993 |
| WO | WO 94/02610 | 2/1994 |
| WO | WO 94/12649 | 6/1994 |
| WO | WO 94/28152 | 12/1994 |
| WO | WO 94/28938 | 12/1994 |
| WO | WO 95/02697 | 1/1995 |
| WO | WO 96/01313 | 1/1996 |
| WO | WO 96/22378 | 7/1996 |

OTHER PUBLICATIONS

Kappel et al., Current Opinion in Biotechnology, vol. 3, p. 548–553, 1992.*
Bradley et al., Bio/Technology, vol. 10, p. 534–539, May 1992.*
Rouy et al., Journal of Biological Chemistry, vol. 273(2), p. 1247–1251, Jan. 9, 1998.*
Duverger et al., Arteriosclerosis, Thrombosis, and Vascular Biology, vol. 16(2), p. 1424–1429, Dec. 1996.*
Duverger et al., Circulation, vol. 94(4), p. 713–717, Aug. 1996.*
Fan et al., Arteriosclerosis, Thrombosis, and Vascular Biology, vol. 15(11), p. 1889–1899, Nov. 1995.*
Palmiter et al., Ann. Rev. Genet., vol. 20, p. 465–499, 1986.*
Heidenreich et al., Molecular Medicine Today, vol. 1(3), p. 128–133, 1995.*
Chapman, M.J., *Methods in Enzymology*, 128, 70–143 (1986).
Chiesa et al., *J. Biol. Chem.*, 267, 24369–24374 (1992).
Gabel et al., *Arterio. Thromb. Vasc. Biol.*, 16, 1559–1567 (1996).
Hughes et al., *Hum. Gene Ther.*, 7, 39–49 (1996).
Maher et al., *Curr. Opin. Lipidol.*, 6, 229–235 (1995).
Menzel et al., *J. Biol. Chem.*, 265,981–986 (1990).
Seddon et al., *Arteriosclerosis*, 7, 113–124 (1987).
Trieu et al., *Biochem. J.*, 309, 899–904 (1995).
Trieu et al., *J. Biol. Chem.*, 270, 15471–15474 (1995).
Utermann et al., *FEBS Let.*, 154, 357–361 (1983).
Utermann et al., *Science*, 246, 904–910 (1989).
Callow et al., *J. Biol. Chem.*, 270, 23914–23917 (1995).
Brunzell et al., *Arteriosclerosis*, 4, 79–93 (1984).
Chen et al., *J. Biol. Chem.*, 261, 12918–12921 (1986).
Chiesa et al., *J. Biol. Chem.*, 268, 23747–23750 (1993).
Fan et al., *Arterioscler. Thromb. Vasc. Biol.*, 15, 1889–1899 (1995).
Frazer et al., *Nat. Gen.*, 9, 424–431 (1995).
Grainger et al., *Nature*, 370, 460–462 (1994).
Karanthanasis, S.K., *Proc. Natl. Acad. Sci. USA*, 82, 6374–6378 (1985).
Karanthanasis et al., *Proc. Natl. Acad. Sci. USA*, 80, 6147–6151 (1983).

(List continued on next page.)

*Primary Examiner*—Scott D. Priebe
*Assistant Examiner*—Shin-Lin Chen
(74) *Attorney, Agent, or Firm*—William C. Coppola

(57) ABSTRACT

A transgenic rabbit which has in its genomic DNA sequences that encode apolipoprotein (a) and apolipoprotein B polypeptides which are capable of combining to produce lipoprotein (a), a process for creating such a rabbit, and the use of the rabbit to identify compounds which are effective in the treatment of human diseases which are associated with, induced and/or exacerbated by Lp(a) expression.

22 Claims, 6 Drawing Sheets

OTHER PUBLICATIONS

Lawn et al., *Nature*, 360, 610–672 (1992).
McCormick et al., *Proc. Natl. Acad. Sci. USA*, 92, 10147–10151 (1995).
Powell et al., *Cell*, 50, 831–840 (1987).
Sharpe et al., *Nucleic Acids Res.*, 12(9), 3917–3932 (1984).
Lebuffe et al., *Biochem. Biophys. Res. Comm.*, 241, 205–211 (1997).
Duverger et al., *Circulation*, 94(4), 713–717 (1996).
Rouy et al., *J. Biol. Chem.*, 273(2), 1247–1251 (1998).
Heidenreich et al., *Molecular Medicine Today*, 1(3), 128–133 (1995).
Purcell–Huynh et al., *J. Clin. Invest.*, 95, 2246–2257 (1995).
Linton et al., *J. Clin. Invest.*, 92, 3029–3037 (1993).
Jaenisch, R., *Science*, 240, 1468–1474 (1988).
Duverger et al., *Arterioscler. Thromb. Vasc. Biol.*, 16, 1424–1429 (1996).
Schultz et al., *Nature*, 365, 762–764 (1993).
Callow et al., *Proc. Natl. Acad. Sci. USA*, 91, 2130–2136 (1994).
Kuehn et al., *Nature*, 326, 295–298 (1987).
Valverius et al., *Molecular Endocrinology*, 3(1), 203–214 (1989).
Brousseau et al., *J. Lipid Research*, 40, 365–375 (1999).
Schultz et al., *Nature*, 365, 762–764 (1993).
Graham et al., *J. Gen. Virol.*, 36, 59–72 (1977).
Levrero et al., *Gene*, 101, 195–202 (1991).
Graham, F.L., *EMBO J.*, 3, 2917–2922 (1984).
Bernstein et al., *Genet. Eng.*, 7, 235–261 (1985).
Robertson et al., *Nature*, 323, 445–448 (1986).
Jahner et al., *Proc. Natl. Acad. Sci. USA*, 82, 6927–6931 (1985).
Jahner et al., *Nature*, 298, 623–628 (1982).
Stewart et al., *EMBO J.*, 6, 383–388 (1987).
Van der Putten et al., *Proc. Natl. Acad. Sci. USA*, 82, 6148–6152 (1985).
Gossler et al., *Proc. Natl. Acad. Sci. USA*, 83, 9065–9060 (1986).
Zoller and Smith, *DNA*, 3, 479–488 (1984).
Jaenich, R., *Proc. Natl. Acad. Sci. USA*, 73, 1260–1264 (1976).
Hutchinson et al., *Proc. Natl. Acad. Sci. USA*, 83, 710–714 (1986).
Oliphant et al., *Gene*, 44, 177–183 (1986).
Reeck et al., *Cell*, 50, 667 (1987).
Rosenfeld et al., *Arteriosclerosis*, 10, 680–687 (1990).
Towbin et al., *Proc. Natl. Acad. Sci. USA*, 6, 4350–4354 (1979).
Laemmli, E.K., *Nature*, 227, 680–685 (1970).
Bender et al., *J. Virol.*, 61, 1639–1646 (1987).
Brinster et al., *Proc. Natl. Acad. Sci. USA*, 82, 4438–4442 (1985).
Bradley et al., *Nature*, 309, 255–258 (1984).
Couto et al., *Nuc. Acid. Res.*, 17(19), 8010 (1989).
Evans et al., *Nature*, 292, 154–156 (1981).
Hutchinson et al., *J. Biol. Chem.*, 253, 6551–6560 (1978).
McCormick, D., *Bio/Technology*, 3(8), 689–693 (1985).

\* cited by examiner

```
         4315           4326                                             4364
                          *
human    PyvFkllKEN  LclnlhkFNE  FiQNeLQEAS  QELQQiHQYI  mALREEYFDP
rabbit   ayivRhmKEN  LyfnlgkFNE  FvQNkLkaAS  QELQQiqQhI  KALRkEYFDP
rat      PfaFkslrEN  iysvfseFNd  FvQsilQEgS  ykLQQvHQYn  KAfREEYFDP
pig      PlgFRllKEN  LdspfgmlNE  FiQNtlwEAS  QELQQlHQYI  KALRkEYFDP
chicken  ahklRslaEN  vkkyisqikn  FsQktlQkls  enLQQlvlYI  KALREEYFDP
```

FIG. 6

TRANSGENIC RABBIT THAT EXPRESSES A FUNCTIONAL HUMAN LIPOPROTEIN (A)

This application is based on and claims priority to U.S. provisional Application No. 60/070,727, filed Jan. 8, 1998.

This invention was made with government support under grant PPG HL18574, awarded by the National Institutes of Health, and Contract No. DE-AC03-76SF00098 between the U.S. Department of Energy and the University of California. The U.S. government has certain rights in the invention.

FIELD OF THE INVENTION

The present invention relates to models of human diseases and to methods of using these models for identifying compounds effective for the treatment of these diseases. In particular, the present invention represents a new experimental model for the in vivo analysis of human lipoprotein (a) [Lp(a)] and the development of therapeutic strategies to reduce the health risks associated with high levels of this lipoprotein.

Dyslipoproteinaemias are disorders in the metabolism of the lipoproteins which are responsible for transporting lipids such as cholesterol and triglycerides in the blood and the peripheral fluids. Dyslipoproteinaemias consequently are associated with life-threatening diseases linked to hypercholesterolaemia, hypocholesterolaemia or hypertriglyceridaemia, such as atherosclerosis.

Atherosclerosis is a complex, polygenic disease which is defined, on the histological plane, by deposits (lipid or fibro-lipid plaques) of lipids and other blood derivatives in the wall of the large arteries (aorta, coronary arteries and carotid). The plaques, which are more or less calcified according to the progress of the disease, can be associated with lesions and are linked to the accumulation, in the arteries, of fatty deposits which essentially consist of cholesterol esters. The plaques are accompanied by a thickening of the arterial wall together with hypertrophy of the smooth muscle, the appearance of foam cells and the accumulation of fibrous tissue. The plaques are raised on the arterial wall resulting in a stenosis, that is, a narrowing or stricture of the artery. In the worst-affected patients, this stenosis is responsible for the vascular occlusions, such as atheroma, thrombosis and embolisms. Accordingly, excess accumulation of cholesterol (hypercholesterolaemias) can lead to very serious cardiovascular diseases such as infarction, sudden death, cardiac decompensation, cerebrovascular diseases, and the like.

It is particularly important, therefore, to have immediately available treatments which diminish, in some disease situations, the levels of plasma cholesterol or stimulate the efflux of cholesterol (reverse transport of cholesterol) from the peripheral tissues in order to unload the cells which have accumulated the cholesterol in the context of forming an atheroma plaque. Cholesterol is transported in the blood by a variety of lipoproteins including the low density lipoproteins (LDL) and the high density lipoproteins (HDL). The LDLs are synthesized in the liver and are responsible for supplying the peripheral tissues with cholesterol. By contrast, the HDLs pick up cholesterol in the peripheral tissues and transport it to the liver where it is stored and/or broken down.

Numerous studies have correlated elevated plasma levels of lipoprotein (a) [Lp(a)] with increased incidence of cardiovascular disease and stroke (reviewed in Utermann, G., Science (1989) 246, 904–910; Maher, V. M. G., & Brown, B. G., Curr. Opin. Lipidol. (1995) 6, 229–235). Lipoprotein(a) is a complex particle composed of a lipid moiety and two disulfide-linked subunits: apolipoprotein B-100 (apoB-100) and apolipoprotein(a) [apo(a)]. The presence of apo(a), a hydrophilic glycoprotein structurally related to plasminogen, distinguishes Lp(a) from low density lipoprotein (LDL) and confers its characteristic biological and physical properties.

Apolipoprotein B-100 (apoB) is the major protein constituent of very low density lipoproteins (VLDL), low density lipoproteins (LDL) and lipoprotein Lp(a). This protein is the physiological ligand of the LDL receptor, and its plasma concentration is positively correlated with the development of atherosclerosis (Brunzell et al. 1984 Arteriosclerosis 4, 79–93). ApoB-100 is one of the largest known proteins, with a mass of 550 kDa and containing 4536 amino acids (Chen et al. 1986 J. Biol. Chem, 261, 12919–21). This apolipoprotein is only synthesized in the liver. Its plasma concentration is 1.0–1.2 g/l. ApoB-100 plays the major role in transporting cholesterol which is synthesized in the liver through the plasma to the other cells of the organism. Another version of apoB, i.e. apoB-48, is present in the chylomicrons. In humans, apoB-48 is synthesized in the intestine. ApoB-48 has a mass of 260 kDa and contains 2152 amino acids which linearly correspond to 48% of the N-terminal end of apoB-100 (Powell et al., 1987, Cell 50, 831–40). Since the C-terminal moiety of apoB-100 contains the zone for binding the apoB-100 to the LDL receptor, apoB-48 does not attach to this latter receptor and behaves in a different manner metabolically.

To study the disease states relating to dyslipoproteinaemias, it is advantageous to have available an animal model which expresses a protein or a protein complex which is associated with a risk for a disease which is linked to dyslipoproteinaemias. Such an animal model would be particularly advantageous for understanding these diseases and, more specifically, the regulatory mechanisms which these proteins or protein complexes initiate. This would make it possible to test, rapidly and in vivo, a considerable number of therapeutic agents or compounds for the purpose of detecting a potential activity associated with the expression of the proteins. Furthermore, such a model would be of interest for developing novel therapeutic methods for treating these types of diseases, such as methods which are based on gene therapy. The in vivo analysis of Lp(a), an independent atherosclerosis risk factor in humans, has been limited in part by its restricted distribution among mammals. Apo(a) is naturally present exclusively in old world monkeys, humans, and one non-primate species, the European hedgehog. Such limited distribution of apo(a) among mammals has limited studies of its in vivo properties.

Accordingly, the present invention relates to animal models of disease states involving Lp(a), including atherosclerosis, to enable screening and identification of compounds for the treatment of these diseases, in particular, atherosclerosis.

Reported Developments

Generally speaking, the murines, namely mice, rats and guinea pigs, are the most widely used animal models. They are easy to manipulate and inexpensive. Unfortunately, these small mammals are not always compatible with the intended application because they are not always representative of humans and their metabolism. Chimpanzees are used for testing therapeutic agents and vaccines directed against various diseases, including AIDS and cancer. However, the very substantial cost incurred in using chimpanzees as a model system constitutes a major and compelling handicap with regard to its use.

Despite the drawbacks of a system using mice, the development of transgenic mice expressing human apo(a) cDNA provided a means to test hypotheses accounting for the effect of Lp(a) on the vasculature. Specifically, these mice have been used to examine the ability of apo(a) to promote atherogenesis by inhibition of plasmin formation and associated consequences (Lawn, et al., Nature (1992) 360, 670–672; Grainger, et al., Nature (1994) 370, 460–462). Studies of apo(a) transgenic mice have also led to several important insights into Lp(a) assembly, including the observation that apo(a) was unable to form a covalent association with LDL containing murine apoB (Chiesa, et al., J Biol Chem (1992) 267, 24369–24374). This result, coupled with evidence for Lp(a) formation when the mice were infused with human LDL or expressed a human apoB transgene (Linton, et al., J Clin Invest (1993) 92, 3029–3037; Callow, et al., Proc Nat'l Acad Sci, USA (1994) 91, 2130–2136) suggested that murine apoB lacked structural requirements necessary for Lp(a) assembly. This was not a completely unexpected finding in light of the absence of the apo(a) gene in mice and the sequence specific interactions between apo(a) and apoB believed to mediate Lp(a) assembly in humans. Two studies using site specific mutagenesis of human apoB transgenes in mice have reported localization of a single cysteine in human apoB (Cys 4326) which provides the site of attachment for apo(a) (Callow, M. J., & Rubin, E. M., J Biol Chem (1995) 270, 23914–23917; McCormick, et al., (1995) 92, 10147–10151).

Most recently, the regulation of apo(a) gene expression has been studied in transgenic mice containing a human apo(a) genomic clone (Frazer, et al., Nat Gen (1995) 9, 424–431). This transgene comprised the apo(a) gene along with its native promoter and cis acting elements present within the approximately 60 kb of 5' and 80 kb of 3' flanking DNA. The transgene was more efficiently expressed (i.e. all the apo[a] transgenic founder lines created containing an intact transgene expressed apo[a]) and resulted in significantly higher plasma apo(a) levels than observed in mice containing an apo(a) cDNA construct. A surprising finding in mice expressing the human apo(a) genomic transgene was the profound sex hormone-induced changes in apo(a) expression, far surpassing the magnitude of androgen and estrogen related changes observed in humans. These changes were, however, qualitatively similar in humans and transgenic mice. In both cases, these hormones lower apo(a) plasma levels.

The use of genomic clones in creating transgenic animals generally has several advantages over the use of cDNA constructs. Most importantly, transgene expression is regulated in an appropriate manner and is independent of its site of integration. This approach has been limited to the production of transgenic mice for large genes such as apo(a), however, due to the technical difficulty of manipulating extremely large genomic clones and the lower efficiency of transgenesis in other animals.

Although transgenic mice have been created containing Lp(a), the small size of the mouse and the differences in lipoprotein profiles between mice and humans has precluded various studies. Accordingly, it is desirable to identify an animal model system which is closer to man but avoids the expense associated with primate model systems.

Thus, there is a need in the art for an appropriate animal model of Lp(a)-mediated diseases and disorders. There is a further need in the art for a transgenic animal, that expresses human Lp(a). Moreover, to be truly useful, a transgenic animal must express the constituent Lp(a) proteins at a high enough level, and must permit covalent association of the constituents so as to produce physiologically relevant levels of Lp(a). To date, the technical difficulties in generating such an animal have not been overcome, until the present invention.

The present invention overcomes these deficiencies of the prior art, by providing a useful transgenic animal that produces physiological levels of human Lp(a), despite the difficulties in achieving such an invention.

In particular, the invention relates to transgenic animals expressing both the human apolipoprotein(a) [apo(a)] and apolipoprotein B (apoB) genes. These animals express human lipoprotein(a) [Lp(a)], the complex particle composed of a lipid moiety and two disulfide-linked subunits of apo(a) and apoB.

SUMMARY OF THE INVENTION

In accordance with the present invention, there is provided a transgenic rabbit which has in its genomic DNA sequences that encode apolipoprotein (a) and apolipoprotein B polypeptides which are capable of combining to produce lipoprotein (a).

The present invention also provides a transgenic rabbit capable of producing lipoprotein (a) wherein the rabbit develops human-like atherosclerotic lesions when fed a cholesterol rich diet.

The present invention also provides for transgenic rabbits capable of producing lipoprotein (a) having exogenous human DNA sequences. The DNA sequences may be selected from genomic DNAs and cDNAs.

As stated above, the transgenic rabbits of the present invention have in their genomic DNA sequences that encode apolipoprotein (a) and apolipoprotein B. The present invention provides transgenic rabbits capable of producing lipoprotein (a) having liver cells which express the DNA sequences and transgenic rabbits capable of producing lipoprotein (a) having testes cells which express the DNA sequences.

Yet another aspect of the present invention is a transgenic rabbit having a stable plasma level of apolipoprotein (a) polypeptide throughout its sexual maturity.

The present invention also provides a process for creating a transgenic rabbit which is capable of expressing apolipoprotein (a) and apolipoprotein B polypeptides and which comprises combining the germ line cells of a first rabbit which is capable of expressing apolipoprotein (a) with the germ cells of a second rabbit which is capable of expressing apolipoprotein B. Germ line cells include, for example, eggs and sperm.

Yet another aspect of the present invention is the provision of a process for creating a transgenic rabbit which is capable of expressing apolipoprotein (a) and apolipoprotein B polypeptides and which comprises mating a first rabbit which is capable of expressing apolipoprotein (a) with another rabbit which is capable of expressing apolipoprotein B.

In a preferred method for creating a transgenic rabbit capable of expressing lipoprotein (a), the rabbit expressing apolipoprotein B protein is provided by injecting a rabbit embryo with a phagemid which contains the human apolipoprotein B gene.

In a preferred method for creating a transgenic rabbit capable of expressing lipoprotein (a), the rabbit expressing apolipoprotein (a) is provided by injecting a rabbit embryo with a yeast artificial chromosome which contains a human apolipoprotein (a) gene.

In yet another method for creating a transgenic rabbit capable of expressing lipoprotein (a), the rabbit expressing apolipoprotein (a) is provided by introducing into a rabbit embryonal stem cell at least one human DNA fragment encoding apolipoprotein (a) protein, combining the stem cell with a rabbit blastocyst and transferring the embryo to a recipient female rabbit.

In yet another method for creating a transgenic rabbit capable of expressing lipoprotein (a), the rabbit expressing apolipoprotein B is provided by introducing into a rabbit embryonal stem cell at least one human DNA fragment encoding apolipoprotein B protein, combining the stem cell with a rabbit blastocyst and transferring the embryo to a recipient female rabbit.

In still yet another method for creating a transgenic rabbit capable of expressing lipoprotein (a), the rabbit carrying and expressing apolipoprotein (a) is provided by infecting a rabbit blastomere with a retrovirus comprising at least one human DNA fragment encoding apolipoprotein (a) protein and transferring the blastomere to a recipient female rabbit.

In yet another method for producing a transgenic rabbit capable of expressing lipoprotein (a), the rabbit carrying and expressing apolipoprotein B is provided by infecting a rabbit blastomere with a retrovirus comprising at least one human DNA fragment encoding apolipoprotein B protein, and transferring the blastomere to a recipient female rabbit.

The present invention also provides a method for determining whether a compound can inhibit a disease or disorder linked to lipoprotein (a) expression or metabolism comprising comparing a first transgenic rabbit which is capable of producing human lipoprotein (a) and manifests a disease or disorder linked to human lipoprotein (a) and which has been treated with the compound, with a second transgenic rabbit which is capable of producing human lipoprotein (a) and manifests a disease or disorder linked to lipoprotein (a) and which has not been treated with the compound. The present invention also provides for utilizing this method wherein the disease or disorder is selected from the group consisting of atherosclerosis, cardiovascular disease, ischemia, stroke, restenosis, coronary artery disease, peripheral occlusive arterial disease, myocardial infarction, thrombosis, and an undesirable lipid profile.

The present invention also provides a method for determining whether a compound can inhibit assembly of a lipoprotein (a) particle comprising comparing the level of lipoprotein (a) production in a first transgenic rabbit which has been treated with said compound and which is capable of producing human lipoprotein (a) to the level of production of lipoprotein (a) in a second transgenic rabbit that has not been treated with said compound and which is capable of producing human lipoprotein (a). The present invention also provides for utilizing this method wherein the compound is selected from the group consisting of antisense nucleic acids, and intracellular binding proteins.

The present invention provides transgenic rabbits, an appropriate animal model of lipoprotein (a)-mediated diseases and disorders. The rabbits express the constituent lipoprotein (a) proteins at a high level so as to facilitate covalent association of the constituents to produce physiologically relevant levels of lipoprotein (a). The rabbits offer significant advantages over transgenic mice, due, in part, to the larger size of the rabbit which facilitates study of vascular injury and restenosis. Furthermore, although rabbits are similar to mice in lacking apolipoprotein (a) and lipoprotein (a), the rabbit's lipoprotein profile more closely mimics that of humans with LDL as the predominant plasma protein. In addition, rabbits also develop well-characterized human-like atherosclerotic lesions when fed a cholesterol-rich diet.

Genomic DNA prepared from founder animals and progeny derived from crossing apo(a) and apoB transgenics was subjected to polymerase chain reaction (PCR) analysis. The apo(a) transgenic founder (sample 2) contained the complete apo(a) genomic clone as judged by amplification with four different primer sets: plasminogen 5' region (PMG 5'), apo(a) 5', apo(a) 3', and apo(a)-like gene 3' (positions indicated below diagram of the genomic clone). ApoB transgenic founders (sample 1) were detected using a single PCR reaction specific for human sequences. Analyses of representative progeny from the apo(a)/apoB matings, shown in samples 3 and 4 (apo(a) only and combined apo(a)/apoB, respectively), confirmed transgene transmission. For each primer set, apo(a) or apoB genomic clone DNA was included as a positive control (sample 5).

Figure 2:
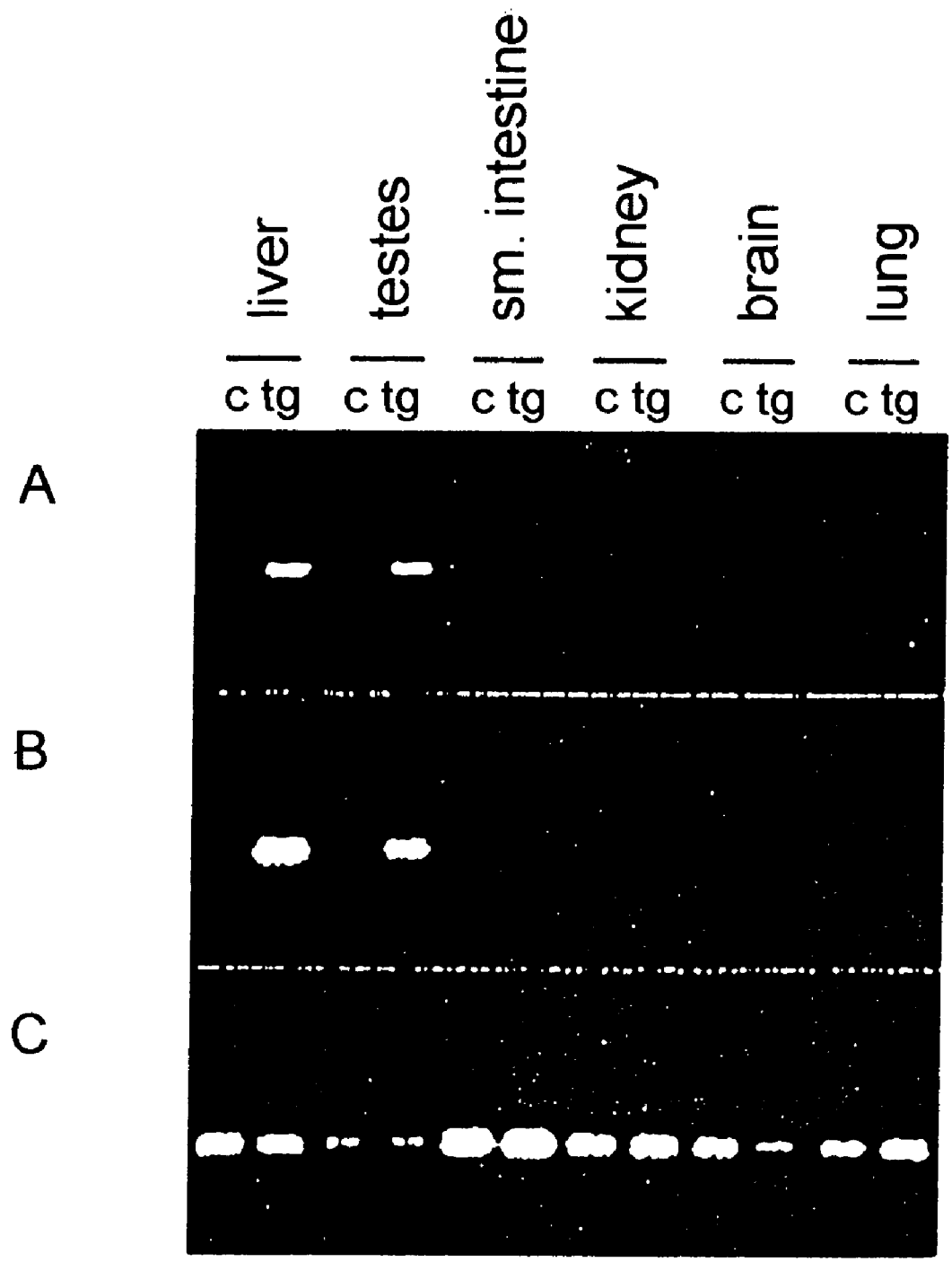

FIG. 2. Tissue distribution of apo(a) and apoB transgene expression.

Expression of apo(a) (panel A) and human apoB (panel B) was analyzed in the indicated tissues of control (c) and transgenic (tg) rabbits by reverse transcriptase-polymerase chain reaction (RT-PCR) analysis. As a control for human apoB specificity, as well as sample quality, rabbit apoB mRNA was also amplified using species specific primers (panel C).

Figure 3:
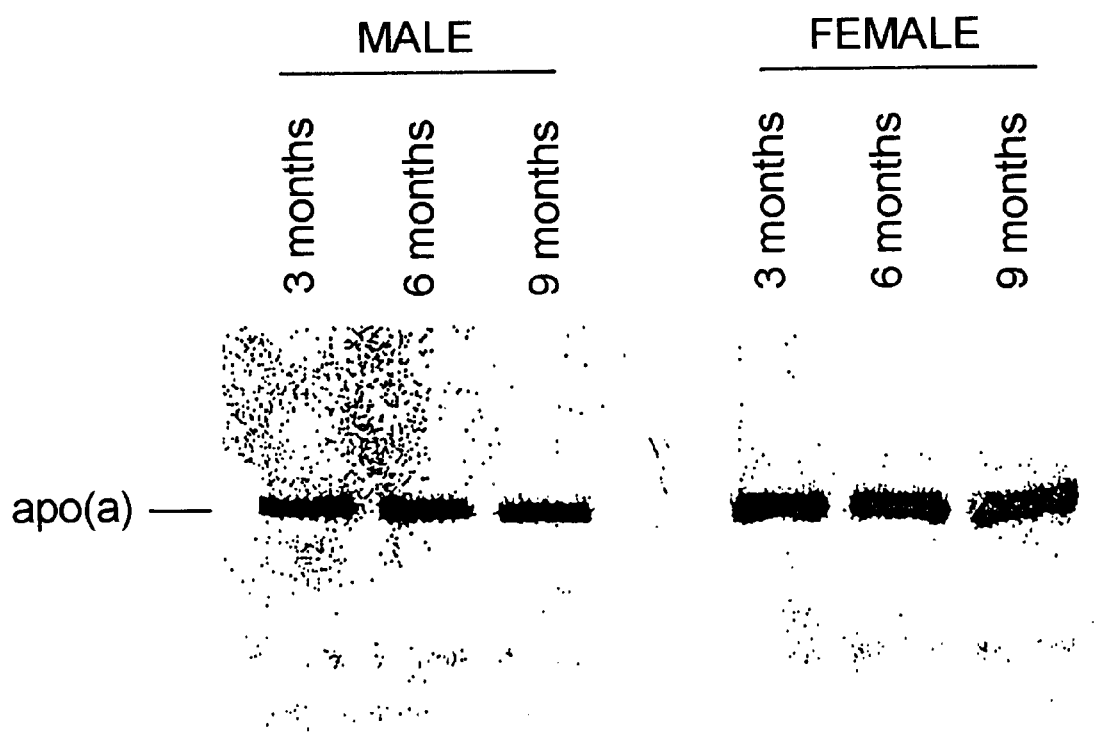

FIG. 3. Time course of apo(a) levels in transgenic rabbits Plasma samples were taken from male and female apo(a) transgenic rabbits at 3 time points after birth: 3, 6, and 9 months. 1 $\mu$L of each sample was subjected to SDS-PAGE under reducing conditions and immunoblotting using antibodies raised against apo(a).

Figure 4:
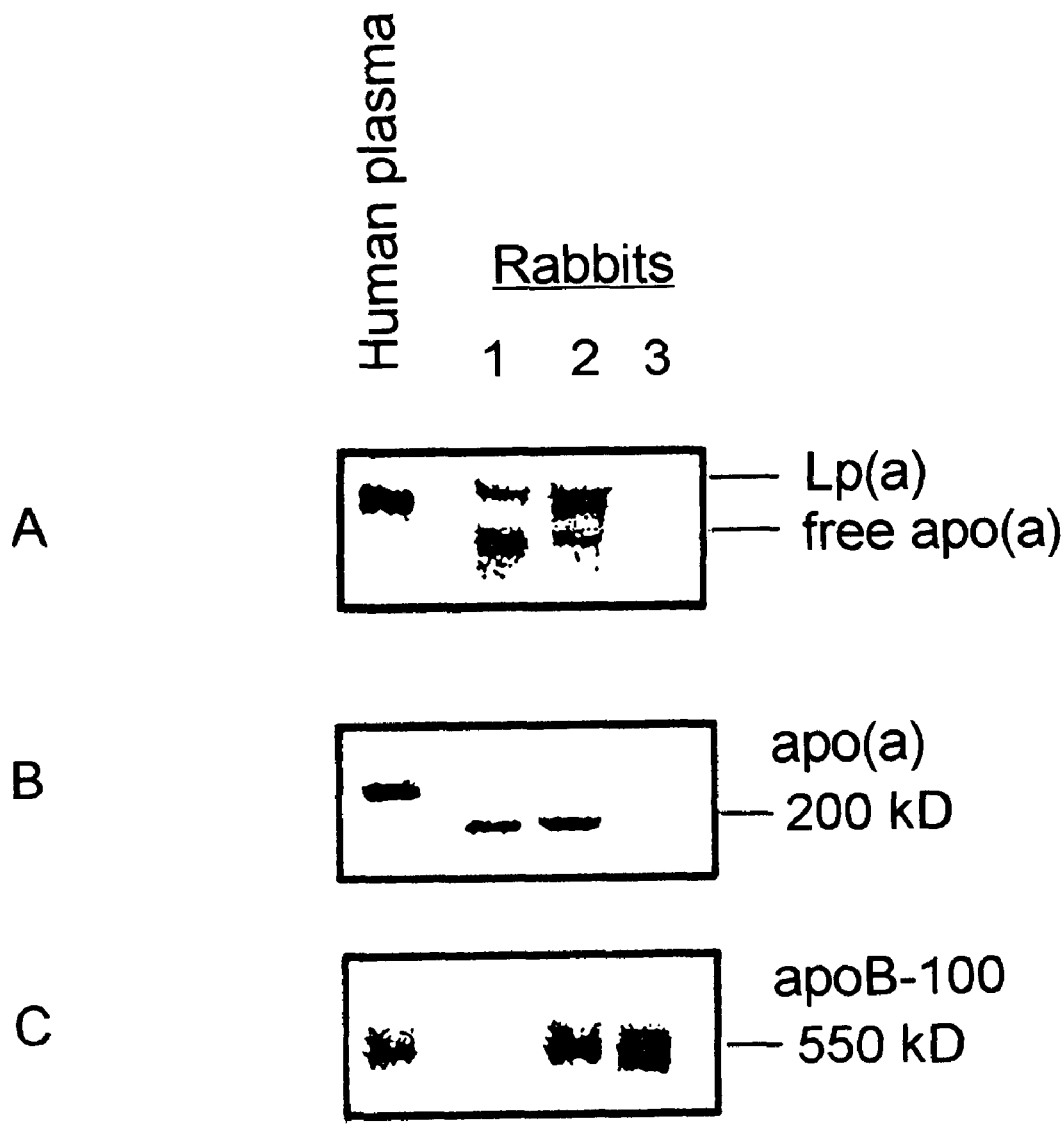

FIG. 4. Immunoblotting of transgenic rabbit plasma Equal volumes of plasma (1$\mu$l) from a human apo(a) transgenic rabbit (1), a human apoB/apo(a) transgenic rabbit (2), and a human apoB transgenic rabbit (3) were size fractionated by SDS-PAGE. Gels were run under non-reducing conditions (panel A) and under reducing conditions (panels B and C). Immunoblotting was performed using antibodies raised against apo(a) (panels A and B) and against human apoB (panel C). Human plasma was included as a control. Sizes of the observed proteins were evaluated using a curve of migrating prestained molecular weight standards vs. migration distance.

Figure 5:
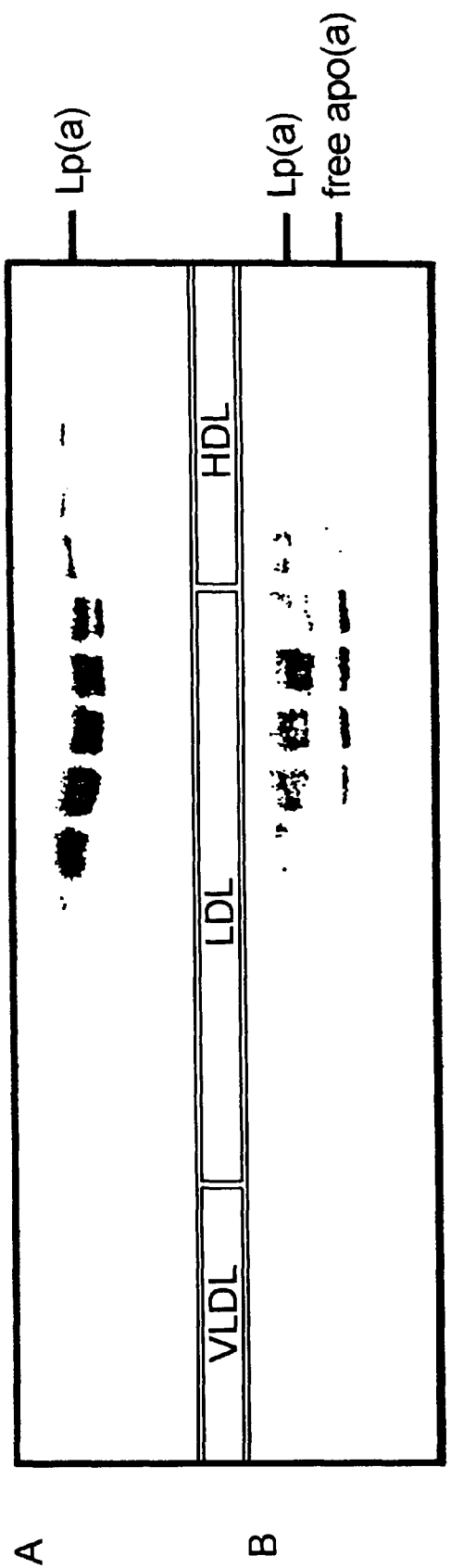

FIG. 5. Immunoblotting of lipoprotein fractions from transgenic rabbits

100 $\mu$L of plasma from human apoB/apo(a) transgenic rabbits (A) or apo(a) transgenic rabbits (B) was size fractionated by chromatography on a Superose 6 column. Even numbered fractions (6–40) were subjected to SDS-PAGE under non-reducing conditions and immunoblotting using antibodies raised against apo(a). Lipoprotein size ranges, determined by cholesterol assay of the fractions, are indicated in the bar between panels A and B.

FIG. 6. Protein sequence alignment of human and rabbit apoB Protein sequence of rabbit apoB (residues 4315–4364; SEQ ID NO:7) aligned with homologous regions of human (SEQ ID NO:8), rat (SEQ ID NO:9), pig (SEQ ID NO:10) and chicken (SEQ ID NO:11) apoB. Sequence identity is indicated by capital letters. Numbering above the sequences corresponds to the human apoB sequence. The * indicates the site of apo(a) attachment to human apoB.

DEFINITIONS

The following defined terms are used throughout the present specification, and should be helpful in understanding the scope and practice of the present invention.

A "polypeptide" is a polymeric compound comprised of covalently linked amino acid residues. Amino acids have the following general structure:

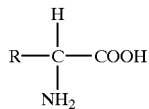

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

A "protein" is a polypeptide which plays a structural or functional role in a living cell. Within the meaning of the present invention, the designation "lipoprotein(a) complex" is understood to cover the apolipoproteins (a) and B as well as Lp(a) and any other proteinaceous product which has an Lp(a) activity. Preferably, the term proteinaceous product denotes any mutant, fragment or peptide which possesses at least one biological property of an apolipoprotein, as well as any natural variant of the apolipoproteins. The polypeptides and proteins of the invention may be glycosylated or unglycosylated.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. Variants also include a related protein having substantially the same biological activity, but obtained from a different species.

The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art.

If such allelic variations, analogues, fragments, derivatives, mutants, and modifications, including alternative mRNA splicing forms and alternative post-translational modification forms result in derivatives of the polypeptide which retain any of the biological properties of the polypeptide, they are intended to be included within the scope of this invention.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence. An 'apo(a) gene' is any gene which encodes an apolipoprotein(a) protein. An 'apoB gene' is any gene which encodes an apolipoprotein B protein. Preferred apo(a) and apoB genes encode human apo(a) and apoB proteins.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins (and their encoding genes) have sequence homology, as reflected by their high degree of sequence similarity.

Accordingly, the term "sequence similarity" in all its grammitical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than about 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The present invention relates to transgenic animals, i.e., rabbits, containing genes encoding analogs and derivatives of apolipoproteins that have the same or homologous functional activity as the apolipoproteins, and homologs thereof from other species. The production and use of derivatives and analogs related to apolipoproteins are within the scope of the present invention. In a specific embodiment, the derivative or analog is functionally active, i.e., capable of exhibiting one or more functional activities associated with a full-length, wild-type apolipoprotein of the invention. In particular, an apolipoprotein derivative of the invention is capable of forming a functional human Lp(a) particle.

Apolipoprotein derivatives can be made by altering encoding nucleic acid sequences by substitutions, additions or deletions that provide for functionally equivalent molecules. Preferably, derivatives are made that have enhanced or increased functional activity relative to native apolipoproteins, i.e., apo(a) and apoB. As used herein, the term "apolipoprotein" refers to apo(a) or apoB.

Due to the degeneracy of nucleotide coding sequences, other DNA sequences which encode substantially the same amino acid sequence as an apolipoprotein gene may be used in the practice of the present invention. These include, but are not limited to, allelic genes, homologous genes from other species, and nucleotide sequences comprising all or portions of apolipoprotein genes which are altered by the substitution of different codons that encode the same amino acid residue within the sequence, thus producing a silent change. Likewise, the apolipoprotein derivatives of the invention include, but are not limited to, those containing, as a primary amino acid sequence, all or part of the amino acid sequence of an apolipoprotein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. Particularly preferred substitutions are:

Lys for Arg and vice versa such that a positive charge may be maintained;

Glu for Asp and vice versa such that a negative charge may be maintained;

Ser for Thr such that a free -OH can be maintained; and

Gln for Asn such that a free $CONH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding apolipoprotein derivatives and analogs of the invention can be produced by various methods known in the art. The manipulations which result in their production can occur at the gene or protein level. For example, the cloned apolipoprotein gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of an apolipoprotein, care should be taken to ensure that the modified gene remains within the same translational reading frame as the native apolipoprotein gene, uninterrupted by translational stop signals, in the gene region where the desired activity is encoded.

Additionally, the apolipoprotein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated apolipoprotein gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Generally, the nucleic acids of the present invention are linked to one or more regulatory regions. Selection of the appropriate regulatory region or regions is a routine matter, within the level of ordinary skill in the art. "Regulatory region" means a nucleic acid sequence which regulates the expression of a second nucleic acid sequence. A regulatory region may include sequences which are naturally responsible for expressing a particular nucleic acid (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

The regulatory regions may comprise a promoter region for functional transcription in endothelial cells, liver, testis, brain or other cell types in which apo(a) and apoB expression is desired, as well as a region situated in 3' of the gene of interest, and which specifies a signal for termination of transcription and a polyadenylation site. All these elements constitute an expression cassette.

"Promoters" that may be used in the present invention include both constituitive promoters and regulated (inducible) promoters. The promoter may be naturally responsible for the expression of the nucleic acid. It may also be from a heterologous source. In particular, it may be promoter sequences of eucaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the promoters of the E1A, MLP, CMV and RSV genes and the like. The non-viral promoter sequences which are preferably used are the ApoAI promoters or the hepatic enhancers of ApoE or the intestinal enhancers of apoCIII. Naturally, these expression sequences can additionally be modified by adding activating sequences, regulatory sequences, etc. The genomic DNA can also be included in a large-capacity expression vector such as the P1 vector or else the YAC, cosmid or plasmid vectors.

In addition, the promoter may be modified by addition of activating or regulatory sequences or sequences allowing a tissue-specific or predominant expression (enolase and GFAP promoters and the like). Moreover, when the nucleic acid does not contain promoter sequences, it may be inserted, such as into the virus genome downstream of such a sequence.

Some promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the contents of which are incorporated herein by reference.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

A "vector" is any means for the transfer of a nucleic acid according to the invention into a host cell. The term "vector" includes both viral and nonviral means for introducing the nucleic acid into a cell in vitro, ex vivo or in vivo. Non-viral vectors include plasmids, phagemids, BAC, PAC, YAC, P1, liposomes, electrically charged lipids (cytofectins), DNA-protein complexes, and biopolymers. The vectors containing a nucleic acid according to the invention may include plasmid, phagemid, P1, BAC, PAC, YAC or cosmid vectors. The vectors of particular interest to the invention include those that are able to accomodate large DNA sequences, (i.e., phagemids, plasmids, P1, BAC, PAC, YAC or cosmid vectors), especially in the case of genomic DNA sequences pertaining to the invention. In addition to a nucleic acid according to the invention, a vector may also contain one or more regulatory regions, and/or selectable markers useful in selecting, measuring, and monitoring nucleic acid transfer results (transfer to which tissues, duration of expression, etc.).

"Lipid profile" means the set of concentrations of cholesterol, triglyceride, lipoprotein cholesterol and other lipids in the body of a human or other animal.

An "undesirable lipid profile" is the condition in which the concentrations of cholesterol, triglyceride, or lipoprotein cholesterol are outside of the age- and gender-adjusted reference ranges. Generally, a concentration of total cholesterol>200 mg/dl, of plasma triglycerides>200 mg/dl, of LDL cholesterol>130 mg/dl, of HDL cholesterol<39 mg/dl, or a ratio of total cholesterol to HDL cholesterol>4.0 is considered to be an undesirable lipid profile. An undesirable lipid profile is associated with a variety of pathological conditions, including hyperlipidaemias, diabetes hypercholesterolaemia, atherosclerosis, and other forms of coronary artery disease.

The down regulation of gene expression using antisense nucleic acids can be achieved at the translational or transcriptional level. Antisense nucleic acids of the invention are preferably nucleic acid fragments capable of specifically hybridizing with a nucleic acid encoding apolipoprotein (a) or B or the corresponding messenger RNAs. These antisense nucleic acids can be synthetic oligonucleotides, optionally modified to improve their stability and selectivity. They can also be DNA sequences whose expression in the cell produces RNA complementary to all or part of the mRNA encoding apolipoprotein (a) or B. Antisense nucleic acids can be prepared by expression of all or part of a nucleic acid encoding apolipoprotein (a) or B, in the opposite orientation, as described in EP 140308. Any length of antisense sequence is suitable for practice of the invention so long as it is capable of down-regulating or blocking expression of apolipoprotein (a) or B. Preferably, the antisense sequence is at least 20 nucleotides in length. The preparation and use of antisense nucleic acids, DNA encoding antisense RNAs and the use of oligo and genetic antisense is disclosed in WO92/15680, the contents of which are incorporated herein by reference.

A "pharmaceutically acceptable carrier" comprises diluents and fillers which are pharmaceutically acceptable for methods of administration, are sterile, and may be aqueous or oleaginous suspensions formulated using suitable dispersing or wetting agents and suspending agents. The particular pharmaceutically acceptable carrier and the ratio of active compound to carrier are determined by the solubility and chemical properties of the composition, the particular mode of administration, and standard pharmaceutical practice.

The term "physiological level" is used herein to refer to a level of protein expression, or Lp(a) production, that results in the transgenic animal possessing a lipoprotein profile closely mimicking that of humans. In particular, the transgenic animal is able to develop well characterized human-like atherosclerotic lesions when fed a cholesterol rich diet. In a specific embodiment, the level of Lp(a) in the transgenic animal is within the range found in humans.

The terms "transgenic animals" and "animal" is used herein to include all vertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extra-chromosomally replicating DNA. The term "germ cell-line transgenic animal" refers to a transgenic animal in which the genetic information was introduced into a germ line cell, thereby conferring the ability to transfer the information to offspring. If such offspring in fact possess some or all of that information, then they, too, are transgenic animals.

DETAILED DESCRIPTION OF THE INVENTION

As discussed hereinabove, there is a need in the art for an appropriate animal model of Lp(a)-mediated diseases and disorders. In particular, it is important to provide an experimental model for the in vivo analysis of human lipoprotein (a). Applicants have obtained for the first time in the art transgenic rabbits capable of providing lipoprotein (a).

Transgenic rabbits represent an increasingly utilized approach to the study of apolipoproteins and their impact on lipoprotein metabolism and atherogenesis (Fan, et al., *Arterioscler Thromb Vasc Biol* (1995) 15, 1889–1899; Duverger, et al., Arterioscler *Thromb Vasc Biol* (1996) 16, 1424–1429). The advantages of this animal, compared to the mouse, relate in part to its relatively larger size, enabling facile studies of vascular injury and restenosis. In addition, while rabbits are similar to mice in lacking apo(a) and Lp(a), their lipoprotein profile more closely mimics that of humans, with LDL as the predominate plasma lipoprotein (Chapman, M. J., in *Methods in Enzymology, vol. 128: Plasma Lipoproteins*, Part A, Preparation, Structure, and *Molecular Biology* Segrest, J. P., & Albers, J. J., Eds. (Academic Press, Inc., New York, 1986), vol. 128, pp. 70–143). Rabbits also develop well characterized human-like atherosclerotic lesions when fed a cholesterol-rich diet.

Within the scope of the present invention, the rabbit has proved to be the appropriate animal model. A comprehensive knowledge exists of the metabolism of the rabbit and of the diseases of this animal which are linked to lipoproteins. The rabbit is an animal which is classified as "LDL mammalian", that is to say the LDLs are the major transporters of plasma cholesterol as in man, contrary to rats and mice, which are animals classified as "HDL mammalian". Furthermore, a large number of genetic variations exist in the lipoproteins within the rabbit lines, such as the WHHL rabbits which are deficient in LDL receptor (Watanabe heritable hyperlipidaemic rabbit) or else the "St Thomas Hospital" rabbits, which overproduce LDLs (Rosenfeld et al., 1990, Arteriosclerosis 10, 680–687; Sedon et al.; 1987, Arteriosclerosis 7, 113–124).

The present invention provides a new, relatively large animal model for studying the biological properties of Lp(a), in the form of a rabbit which contains both human genomic transgenes for apo(a) or apoB. The rabbits demonstrate efficient, tissue specific expression of both human transgenes and the assembly of Lp(a) particles. In addition, apo(a) covalently interacts in vivo with rabbit apoB and the transgenic rabbit model represents a means to characterize this novel interaction. Applicants have prepared a transgenic rabbit into whose genome has been inserted exogenous genomic DNA sequences which encode apolipoprotein(a) and apolipoprotein B proteins which form a lipoprotein(a) complex.

In addition to providing unique insights into Lp(a) assembly and apo(a) expression, several features of the Lp(a) transgenic rabbits provided by this invention represent improvements over currently available animal models for investigating Lp(a). These animals possess a lipoprotein profile closely mimicking that of humans and develop well characterized human-like atherosclerotic lesions when fed a cholesterol-rich diet. Also, due to their relatively large size, they have been successfully used in vascular injury and restenosis studies. Thus, these transgenic rabbits will provide a valuable resource to study factors affecting Lp(a) levels as well as the effects of Lp(a) on the progression of atherosclerosis and vascular disease.

Any rabbit can be used to prepare a transgenic animal of the invention. Preferably, the rabbit is a homogeneous laboratory strain, which can be obtained from any animal source such as Charles River or Jackson Laboratories (Bar Harbor, Maine). In a specific embodiment, infra, the rabbit is a New Zealand White rabbit. Alternatively, a Watanabe hyperlipidemic transgenic rabbit of the invention can be generated.

In a preferred embodiment, the present invention provides a process for creating the transgenic rabbit by injecting, into a rabbit embryo, exogenous genomic DNA sequences encoding apo(a) or apoB proteins which form a lipoprotein (a) complex, transferring the embryo to a recipient rabbit and, after the birth, checking for the presence of the genomic DNA sequences in the genome of the neonate rabbits. Apo(a) transgenic rabbits and apoB transgenic rabbits are then mated to produce the apo(a)-apoB transgenic rabbit which expresses Lp(a).

The process for creating the transgenic rabbit is described in more detail in Example 2 below. The implementation of such a process does not present any difficulties to the skilled person who is familiar with the techniques of microinjection, and removal and implantation of embryos, as well as animal husbandry.

The present invention especially relates to the use of a 270 kb yeast artificial chromosome (YAC) clone which contains the human apo(a) gene and a 90 kb P1 phagemid clone which contains the human apoB gene to create a transgenic rabbit which expresses both transgenes. The transgenic rabbit of the present invention exhibits tissue-specific expression of both transgenes which is localized predominantly in the liver. In contrast to observations in apo(a) transgenic mice, the current invention results in apo(a) plasma levels that are stable throughout sexual maturity in the rabbits. In addition, apo(a) is able to form a covalent association with the endogenous rabbit apoB, albeit with a lower efficiency than its association with human apoB. The invention of this Lp(a) transgenic rabbit model provides for new insights into the structural requirements for Lp(a) assembly and regulation of apo(a) expression. In addition, these transgenic rabbits represent a new experimental model for the in vivo analysis of Lp(a) and the development of therapeutic strategies to reduce atherosclerosis risk associated with high levels of this lipoprotein.

Accordingly, the present invention provides a transgenic rabbit comprising both apo(a) and apoB genes or variants thereof, and the rabbit is capable of expressing these genes such that a lipoprotein(a) complex is formed.

The genetic information present in the transgenic rabbits may be foreign to the species of animal to which the recipient belongs, (i.e. exogenous) foreign only to the particular individual recipient (i.e exogenous), or genetic information already possessed by the recipient. In the last case, the introduced gene may be differently expressed compared to the native endogenous gene.

The genes may be obtained by isolating them from genomic sources, by preparation of cDNAs from isolated RNA templates, by directed synthesis, or by some combination thereof. In a preferred embodiment of the invention, the human apo(a) and apoB genes are cloned from genomic DNA, such that the transgenes' expression is regulated in an appropriate manner and is independent of its site of integration into the transgenic animal's chromosomal DNA.

A transgenic rabbit according to the invention can integrate the genomic DNA sequences into all its cells or only into a certain percentage of cells; in the latter case it would be termed mosaic. In general, the genomic DNA sequences are integrated into all the cells. The inserted genomic DNA sequences according to the invention encode all, or an active part, of the proteins which are involved in lipoprotein(a) complex formation and/or metabolism. These genomic DNA sequences can also contain several genes which are organized, if need be, in cluster form.

Those inserted DNA sequences within the meaning of the present invention which may more specifically be cited are the genes which encode all or an active part of apolipoproteins (a), B, or a variant or a derivative of these apolipoproteins, and form an Lp(a) complex.

To be expressed, a gene should be operably linked to a regulatory region. Regulatory regions, such as promoters, may be used to increase, decrease, regulate or designate to certain tissues or to certain stages of development the expression of a gene. The promoter need not be a naturally occurring promoter. The "transgenic non-human animals" of the invention are produced by introducing "transgenes" into the germline of the non-human animal. The methods enabling the introduction of DNA into cells are generally available and well-known in the art. Different methods of introducing transgenes could be used. Generally, the zygote is the preferred target for microinjection. The use of zygotes as a target for gene transfer has a major advantage. In most cases, the injected DNA will be incorporated into the host gene before the first cleavage (Brinster, et al., (1985) *Proc. Natl. Acad. Sci.* USA 82, 4438–4442). Consequently, nearly all cells of the transgenic non-human animal will carry the incorporated transgene. Generally, this will also result in the efficient transmission of the transgene to offspring of the founder since 50% of the germ cells will harbor the transgene. Microinjection of zygotes is a preferred method for incorporating transgenes in practicing the invention.

Retroviral infection can also be used to introduce a transgene into a non-human animal. The developing non-human embryo can be cultured in vitro to the blastocyst stage. During this time, blastomeres may be targets for retroviral infection (Jaenich, R. (1976) *Proc. Natl. Acad. Sci.* USA 73, 1260–1264). Efficient infection of the blastomeres is obtained by enzymatic treatment to remove the zona pellucida (Hogan et al., (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner et al., (1985) *Proc. Natl. Acad. Sci.* USA 82, 6927–6931; Van der Putten et al., (1985) *Proc. Natl. Acad. Sci.* USA 82, 6148–6152). Transfection is easily and efficiently obtained by culturing the blastomeres on a monolayer of virus-producing cells (Van der Putten et al., (1985) *Proc. Natl. Acad. Sci.* USA 82, 6148–6152; Stewart et al., (1987) EMBO J. 6:383–388). Alternatively, infection can be performed at a later stage. Virus or virus-producing cells can be injected into the blastocoele (Jahner et al., (1982) *Nature* 298:623–628.). Most of the founder animals will be mosaic for the transgene since incorporation occurs only in a subset of the cells which formed the transgenic non-human animal. Furthermore, the founder animal may contain retroviral insertions of the transgene at a variety of positions in the genome; these generally segregate in the offspring. In addition, it is also possible to introduce transgenes into the germ line, albeit with low efficiency, by intrauterine retroviral infection of the midgestation embryo (Jahner et al., (1982) *Nature* 298:623–628.).

A third type of target cell for transgene introduction is the embryonal stem cell (ES). ES cells are obtained from pre-implantation embryos cultured in vitro (Evans, M. J., et al., (1981) *Nature* 292, 154–156; Bradley, A., et al. (1984) *Nature* 309, 255–258; Gossler, et al., (1986) *Proc. Natl. Acad. Sci.* USA 83, 9065–9060; and Robertson, et al., (1986) *Nature* 322, 445–448). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal (For review see Jaenisch, R. (1988) *Science* 240, 1468–1474).

The methods for evaluating the presence of the introduced DNA as well as its expression are readily available and well-known in the art. Such methods include, but are not limited to DNA (Southern) hybridization to detect the exogenous DNA, polymerase chain reaction (PCR), polyacrylamide gel electrophoresis (PAGE) and Western blots to detect DNA, RNA and protein.

Rabbits which possess sequences encoding human apolipoprotein (a) in its genomic DNA, including its germ line DNA, are mated with rabbits which possess human apolipoprotein B in its genomic DNA, including its germ line DNA. In a specific embodiment, a transgenic rabbit that expresses apo-B can be mated with a transgenic rabbit that expresses physiological levels of apo(a), as described in WO 95/25793 and allowed U.S. patent application Ser. No. 08/704,582, now U.S. Pat. No. 5,792,902, issued Aug. 11, 1998, the specification of which is incorporated herein by reference in its entirety. The resultant progeny are then screened to identify those rabbits which express apolipoprotein (a) and apolipoprotein B, such that lipoprotein (a) is produced.

As used herein, a "transgene" is a DNA sequence introduced into the germline of a non-human animal by way of human intervention such as by way of the Examples described below.

Nucleic Acids

Transgenic animals according to the invention comprise nucleic acid sequences comprising genes encoding apo(a) and apoB or variants thereof and are capable of expressing these genes to form a lipoprotein(a) complex. The nucleic acid may be of natural or artificial origin. It may be genomic DNA (gDNA), complementary DNA (cDNA), hybrid sequences or synthetic or semisynthetic sequences. It may be of human, animal, plant, bacterial or viral origin and the like. It may be obtained by any technique known to persons skilled in the art, and especially by screening libraries, by chemical synthesis, or alternatively by mixed methods including chemical or enzymatic modification of sequences obtained by screening libraries. It is preferably cDNA or gDNA.

A YAC clone containing the human apo(a) gene (clone 366H2 in the CEPH library) has previously been described (Frazer, K. A., Narla, G., Zhang, J. L., & Rubin, E. M., Nat Gen (1995) 9, 424–431). To isolate the human apo(a) gene, the YAC can be separated from the yeast chromosomes by pulse field gel electrophoresis. The band containing the YAC is then excised from SeaPlaque GTG agarose (FMC, Rockland, Md.), treated with beta-agarase (NEB, Beverly, Mass.), and dialyzed against 0.1M NaCl, 10 mM Tris, 0.1 mM EDTA (Couto, L. B., Spangler, E. A., & Rubin, E. M., NucAcid Res (1989) 17(19), 8010).

A 90 kb P1 phagernid containing the human apoB gene has been previously described (Callow, et al., *Proc Nat'l Acad Sci, USA* (1994) 91, 2130–2136). Alternatively, a DNA fragment containing the nucleic acid sequence encoding human apo(a) or apoB under the control of its own promoter can be obtained by screening human genomic or cDNA expression libraries. To do this, the library is screened by hybridization with a DNA probe which was complementary to human apolipoprotein(a) or apoB. The apo(a) or apoB DNA-containing clone(s) isolated in this screening are then analyzed by comparison with their respective published sequences (Frazer, K. A., Narla, G., Zhang, J. L., & Rubin, E. M., Nat Gen (1995) 9, 424–431; and Callow, et al., *Proc Nat'l Acad Sci, USA* (1994) 91, 2130–2136).

Regulatory Regions

Generally, the genes encoding apo(a) and apoB or variants thereof are linked to one or more regulatory regions. Selection of the appropriate regulatory region or regions is a routine matter that is within the level of ordinary skill in the art.

The regulatory regions may comprise a promoter region for functional transcription, as well as a region situated in 3' of the gene of interest, and which specifies a signal for termination of transcription and a polyadenylation site. All these elements constitute an expression cassette.

Promoters that may be used in the present invention include both constituitive promoters and regulated (inducible) promoters. The promoter may be naturally responsible for the expression of the nucleic acid. It may also be from a heterologous source and may be promoter sequences of eucaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the promoters of the E1A, MLP, HCMV and RSV genes and the like. In addition, the promoter may be modified by addition of activating or regulatory sequences or sequences allowing a tissue-specific or predominant expression. Tissue specific promoters provide the means for modeling a variety of diseases. When the nucleic acid does not contain promoter sequences, one may be inserted.

Additional promoters useful for practice of this invention are the ubiquitous promoters HPRT vimentin, actin and tubulin the intermediate filament promoters desmin neurofilaments, keratin, and GFAP; the therapeutic gene promoters MDR, CFTR, and factor VIII promoters which are preferentially activated in dividing cells; promoters which respond to a stimulus such as steroid hormone receptor and retinoic acid receptor promoters; tetracycline-regulated transcriptional modulators; cytomegalovirus immediate-early; retroviral LTR metallothionein; SV40, E1a and MLP promoters. Tetracycline-regulated transcriptional modulators and CMV promoters are described in WO 96/01313, U.S. Pat. No. 5,168,062 and 5,385,839, the contents of which are incorporated herein by reference.

In certain embodiments of the invention, the human apo(a) and apoB genes or variants thereof are operably linked to a strong promoter, for example, a human cytomegalovirus (HCMV) promoter, so that high levels of transgene expression are acheived. A transgenic animal comprising such constructs would provide a model of human lipoprotein(a) expression and, therefore, of atherosclerosis, stroke, ischemia, restenosis, cardiovascular disease, coronary artery disease, pheripheral occlusive arterial disease, myocardial infarction, undesirable lipid profile, and thrombosis as well.

In another embodiment of the invention, the human apo(a) and apoB genes are operably linked to tissue specific promoter(s) in order to localize overexpression of the transgenes to particular cells. Preferred tissue specific promoters include vasculation and endothelial cells.

It is also possible to overexpress the human apo (a) and apo B genes operably linked to a sequence encoding a mutated ligand binding domain from a glucocorticoid or estrogen receptor fused to the genes. In this embodiment, expression of the genes is regulated by glucocorticoids or tamoxifen.

Vectors

As discussed above, a "vector" is any means for the transfer of a nucleic acid into a host cell. Preferred vectors are plasmids and viral vectors, such as, for example, retroviruses.

Viral vectors may be used to produce a transgenic animal according to the invention. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents.

Preferably, the replication defective virus retains the sequences of its genome which are necessary for encapsidating the viral particles.

The retroviruses are integrating viruses which infect dividing cells. The retrovirus genome includes two LTRs, an encapsidation sequence and three coding regions (gag, pol and env). The construction of recombinant retroviral vectors has been described: see, in particular, EP 453242, EP178220, Bernstein et al. Genet. Eng. (1985) 7:235; McCormick, BioTechnology (1985) 3: 689 etc. In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("Moloney murine leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm–12 cell line (WO89/07150). In addition, the recombinant retroviral vectors can contain modifications within the LTRs for suppressing transcriptional activity as well as extensive encapsidation sequences which may include a part of the gag gene (Bender et al., J. Virol. (1987) 61: 1639). Recombinant retroviral vectors are purified by standard techniques known to those having ordinary skill in the art.

Drua Screening Assays

Transgenic animals overexpressing the human apo(a) and apoB genes or variants thereof are useful in drug screening assays. These assays are useful for identifying compounds effective for the treatment of diseases, such as atherosclerosis, stroke, ischemia, restenosis, cardiovascular disease, coronary artery disease, pheripheral occlusive arterial disease, myocardial infarction, undesirable lipid profile, thrombosis and the like.

The present invention provides methods of determining the ability of a compound to modulate apo(a), apoB and lipoprotein(a) functions in a cell. Preferred methods comprise administering a compound to a transgenic non-human animal comprising the human apo(a) and apoB genes or variants thereof which are expressed and form a human lipoprotein(a) complex and comparing the potential therapeutic effects of the compound in the transgenic animals compared to that in control animals. Potential therapeutic compounds that prevent and/or treat the diseases or disorders that are associated with, induced and/or exacerbated by Lp(a) expression, for example, atherosclerosis, restenosis, stroke, ischemia, restenosis, cardiovascular disease, coronary artery disease, pheripheral occlusive arterial disease, myocardial infarction, undesirable lipid profile, and thrombosis and the like may be determined.

The present invention also relates to the use of the claimed transgenic rabbit for detecting the activity of therapeutic agents/compounds or therapeutic methods with a view to preventing and/or treating diseases linked to Lp(a) expression as well as to the methods for detecting novel compounds using this rabbit and to the compounds which are thus characterized. This transgenic rabbit animal model system is particularly advantageous for detecting specific therapeutic agents/compounds for treating and/or preventing diseases linked to Lp(a) expression and/or metabolism, in particular in the field of cardiovascular diseases such as atherosclerosis, cardiovascular disease, coronary artery disease, stroke, ischemia, peripheral occlusive arterial disease, restenosis, thrombosis, myocardial infarction, angina pectoris, sudden death, an undesirable lipid profile, cardiac decompensation or cerebrovascular diseases.

The invention also provides methods for identifying a compound effective for the treatment of diseases and disorders associated with, induced and/or exacerbated by Lp(a) expression, such as atherosclerosis, restenosis, stroke, ischemia, restenosis, cardiovascular disease, coronary artery disease, pheripheral occlusive arterial disease, myocardial infarction, undesirable lipid profile, and thrombosis and the like. Such methods comprise administering a compound to a transgenic non-human animal comprising the human apo (a) and apoB genes or variants thereof, wherein the transgenes are expressed and form a human lipoprotein(a) complex, and comparing the potential therapeutic effects of the compound in the transgenic animals compared to that in control transgenic animals.

The present invention also provides a method for identifying a compound that is able to modulate human Lp(a) assembly in a cell by administering a compound to a transgenic non-human animal comprising the human apo(a) and apoB genes or variants thereof, wherein the transgenes are expressed and form a human lipoprotein(a) complex, and monitoring the human Lp(a) levels and/or biological activity within the treated transgenic animal as compared to that in control transgenic animals. In a preferred aspect of the invention, the cells are cells of an animal suffering from a disease or disorder associated with, induced and/or exacerbated by Lp(a) expression and the method comprises administering to the cells of an animal a compound capable of modulating Lp(a) function to prevent and/or treat the disease/disorder. Such diseases include atherosclerosis, restenosis, stroke, ischemia, restenosis, cardiovascular disease, coronary artery disease, pheripheral occlusive arterial disease, myocardial infarction, undesirable lipid profile, and thrombosis and the like.

The drug screening assays of the invention may be performed on a large scale or small scale. Large scale screening involves visual observation of the vasculature or other tissue expressing the apo(a) and apoB transgenes, and comparison to control animals. For example, if the human Lp(a) production within the transgenic animal results in atherosclerotic plaque formation in the blood vessels, the observer would evaluate a drug candidate based on its ability to decrease this formation relative to untreated animals.

Alternatively, the transgenic animals of the invention that express human Lp(a) or a variant thereof and also comprise a reporter gene operably linked to a promoter whose expression is altered by Lp(a) or a variant thereof may be prepared. For example, such a promoter operably linked to the β-galactosidase gene (LacZ) would be uninduced or induced depending on the respective presence or absence of corrective treatment for Lp(a) expression.

Drug screening assays of the invention can also be performed on a small scale. Small scale assays involve biopsy and either histological and/or immunohistochemical analyses. These characteristics can be evaluated histologically by a skilled practioner. Immunohistochemical analysis can be performed using a marker for atherosclerosis, stroke, ischemia, restenosis, cardiovascular disease, coronary artery disease, pheripheral occlusive arterial disease, myocardial infarction, undesirable lipid profile, thrombosis and the like.

Compounds capable of modulating Lp(a) function include those that are capable of inhibiting or down-regulating the expression of either or both of the apo(a) and apoB genes, of inhibiting the formation of the Lp(a) complex or the biological activity of Lp(a) in a cell, or reducing the plasma level of lipoprotein(a). Such compounds include antisense nucleic acids, intracellular binding proteins, including antibodies and any compound, natural or synthetic identified by using the transgenic animals and assays escribed herein.

Preparation and use of antisense polynucleotides, DNA encoding antisense RNA molecules and use of oligonucleotide and genetic antisense are disclosed in WO 92/15680, the entire contents of which are incorporated herein by reference. Antisense nucleic acids for use according to the invention are preferably RNA capable of specifically hybridizing with all or part of the apo(a) and/or apoB genes, or their corresponding messenger RNAs. The antisense sequence may be derived from DNA sequences whose expression in the cell produces RNA complementary to all or part of the apo(a) and/or apoB genes. These antisense sequences can be prepared by expression of all or part of a sequence encoding apo(a) and/or apoB in the opposite orientation. Any length of the antisense sequence is suitable for practice of the invention so long as it is capable of down-regulating or blocking expression of the apo(a) and/or apoB genes. Preferably, the antisense sequence is at least 20 nucleotides in length.

In one aspect, the nucleic acid encodes antisense RNA molecules. In this embodiment, the nucleic acid is operably linked to suitable regulatory regions (discussed above) enabling expression of the nucleic acid sequence, and is introduced into a cell utilizing, preferably, recombinant vector constructs, which will express the antisense nucleic acid once the vector is introduced into the cell. Examples of suitable vectors includes plasmids, adenoviruses, adeno-associated viruses (see WO 91/18088; WO 93/09239; U.S. Pat. No. 4,797,368, U.S. Pat. No. 5,139,941, EP 488 528), retroviruses (see above), and herpes viruses. For delivery of a therapeutic gene, the vector is preferably an adenovirus.

Adenoviruses are eukaryotic DNA viruses that can be modified to efficiently deliver a nucleic acid of the invention to a variety of cell types.

Various serotypes of adenovirus exist. of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine, ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors for use in the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1–L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein by reference).

The replication defective recombinant adenoviruses can be prepared by any technique known to the person skilled in the art (Levrero et al., (1991) Gene 101, 195; EP 185 573; Graham, (1984) EMBO J. 3, 2917). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., (1977) J. Gen. Virol. 36, 59) which contains the left-hand portion of the genome of an Ad5 adenovirus (12%) integrated into its genome, and cell lines which are able to complement the E1 and E4 functions, as described in applications WO94/26914 and W095/02697. Recombinant adenoviruses are recovered and purified using standard molecular biological techniques, which are well known to one of ordinary skill in the art.

Another embodiment of the method of the invention to specifically inhibit Lp(a) activity comprises inhibiting Lp(a) function by expression of a nucleic acid sequence encoding an intracellular binding protein capable of selectively interacting with apo(a), apoB and/or the Lp(a) complex within a transfected cell. WO 94/29446 and WO 94/02610, the entire contents of which are incorporated herein by reference, disclose cellular transfection with genes encoding an intracellular binding protein. An intracellular binding protein includes any protein capable of selectively interacting, or binding, with apo(a), apoB and/or the Lp(a) complex, including human apo(a), apoB and/or Lp(a) in the cell in which it is expressed and of neutralizing the function of bound apo(a), apoB and/or Lp(a). Preferably, the intracellular binding protein is an antibody or a fragment of an antibody. Preferably, the intracellular binding protein is a single chain antibody. The antibody can be monoclonal or polyclonal.

WO 94/02610 discloses preparation of antibodies and identification of the nucleic acid encoding a particular antibody. Using the apo(a), apoB or Lp(a) complex proteins or fragments thereof, a monoclonal antibody specific for apo(a), apoB or Lp(a) is prepared according to techniques known to those skilled in the art. A vector comprising the nucleic acid encoding an intracellular binding protein, or a portion thereof, and capable of expression in a host cell is subsequently prepared for use in the method of this invention. Suitable vectors and methods of delivering nucleic acids encoding intracellular binding proteins to cells containing apo(a), apoB and/or Lp(a) include those discussed above for delivery of antisense nucleic acids.

In a preferred aspect of this embodiment, the nucleic acid sequence encoding an apo(a), apoB and/or Lp(a) intracellular binding protein additionally comprises a sequence encoding 1) a localization signal for targeting the intracellular binding protein to an appropriate cellular location to permit interaction of the intracellular binding protein and its target molecule(s), and/or 2) a sequence enabling insertion of the intracellular binding protein in the plasma membrane. The localization signal or insertion sequence can be located anywhere on the intracellular binding protein, so long as it does not interfere with the proteinos ability to bind to apo(a), apoB and/or Lp(a). Examples of localization signals are disclosed in WO 94/02610.

Pharmaceutical Compositions

Compounds capable of modulating Lp(a) function include antisense nucleic acids, intracellular binding proteins and compounds identified using the transgenic animals and assays described herein.

Antisense nucleic acid constructs that are capable of down-regulating or blocking expression of the apo(a) and apoB transgenes may be delivered to affected cells. The nucleic acids, either in the form of a vector or naked DNA, may be combined with one or more pharmaceutically acceptable carriers for an injectable formulation. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, allow the constitution of injectable solutions.

The preferred sterile injectable preparations can be a solution or suspension in a nontoxic parenterally acceptable solvent or diluent. Examples of pharmaceutically acceptable carriers are saline, buffered saline, isotonic saline (e.g. monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or diglycerides. Fatty acids such as oleic acid also find use in the preparation of injectables.

If administered as a virus the dose(s) may be adapted as a function of various parameters, and in particular as a function of the site of administration considered, the number of injections, the gene to be expressed or alternatively the desired duration of treatment. In general, recombinant adenoviruses are formulated and administered in the form of doses of between $10^4$ and $10^{14}$ pfu, and preferably $10^6$ to $10^{11}$ pfu. The term pfu (plaque forming unit) corresponds to the infectivity of a virus solution, and is determined by infecting an appropriate cell culture and measuring, generally after 15 days, the number of plaques of infected cells.

The technique for determining the pfu titre of a viral solution are well documented in the literature.

A nucleic acid, such as that encoding an antisense or intracellular binding protein, can also be administered as a naked DNA. Methods for formulating and administering naked DNA to mammalian muscle tissue are disclosed in U.S. Pat. Nos. 5,580,859 and 5,589,466, the contents of which are incorporated herein by reference.

EXAMPLES

The present invention will be described in greater detail with the aid of the following examples which should be considered as illustrative and nonlimiting.

General Molecular Biology

In accordance with the present invention, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. ÊHiggins eds. (1985)]; Transcription And Translation [B. D. Hames & S. J. Higgins, eds. (1984)]; *Animal Cell Culture* [R. I. Freshney, ed. (1986)]; *Immobilized Cells And Enzymes* [IRL Press, (1986)]; B.ÊPerbal, *A Practical Guide To Molecular Cloning* (1984); F. M. Ausubel et al. (eds.), *Current Protocols in Molecular Biology*, John Wiley & Sons, Inc. (1994).

Example 1

Human apo(a) and apo B DNA Preparation and Characterization

The YAC clone containing the human apo(a) gene (clone 366H2 in the CEPH library) has previously been described (Frazer, K. A., Narla, G., Zhang, J. L., & Rubin, E. M., Nat Gen (1995) 9, 424–431). The YAC was separated from the yeast chromosomes by pulse field gel electrophoresis. The band containing the YAC was excised from SeaPlaque GTG agarose (FMC, Rockland, Md.), treated with beta-agarase (NEB, Beverly, Mass.), and then dialyzed against 0. IM NaCl, 10 mM Tris, 0.1 mM EDTA (Couto, L. B., Spangler, E. A., & Rubin, E. M., Nuc Acid Res (1989) 17(19), 8010). The 90 kb P1 phagemid containing the human apoB gene has been previously described (Callow, et al., *Proc Nat'l Acad Sci, USA* (1994) 91, 2130–2136).

Example 2

Production and Screening of Transgenic Rabbits

The production of transgenic rabbits utilized the methods previously described by (Duverger, et al., *Arterioscler Thromb Vasc Biol* (1996) 16, 1424–1429). Briefly, New Zealand White adult female rabbits were superovulated, then mated on the same day that luteinizing hormone was injected. Embryos were collected 17 hours later. Embryo injection, transfer to pseudopregnant females and animal husbandry was as previously reported (Fan, et al., *Arterioscler Thromb Vasc Biol* (1995) 15, 1889–1899); Duverger, et al., *Arterioscler Thromb Vasc Biol* (1996) 16, 1424–1429). Approximately 2 µL of 1 ng/ml DNA solution containing either the human apo(a) YAC or the human apoB P1 phagemid was injected into the male pronuclei.

Figure 1:
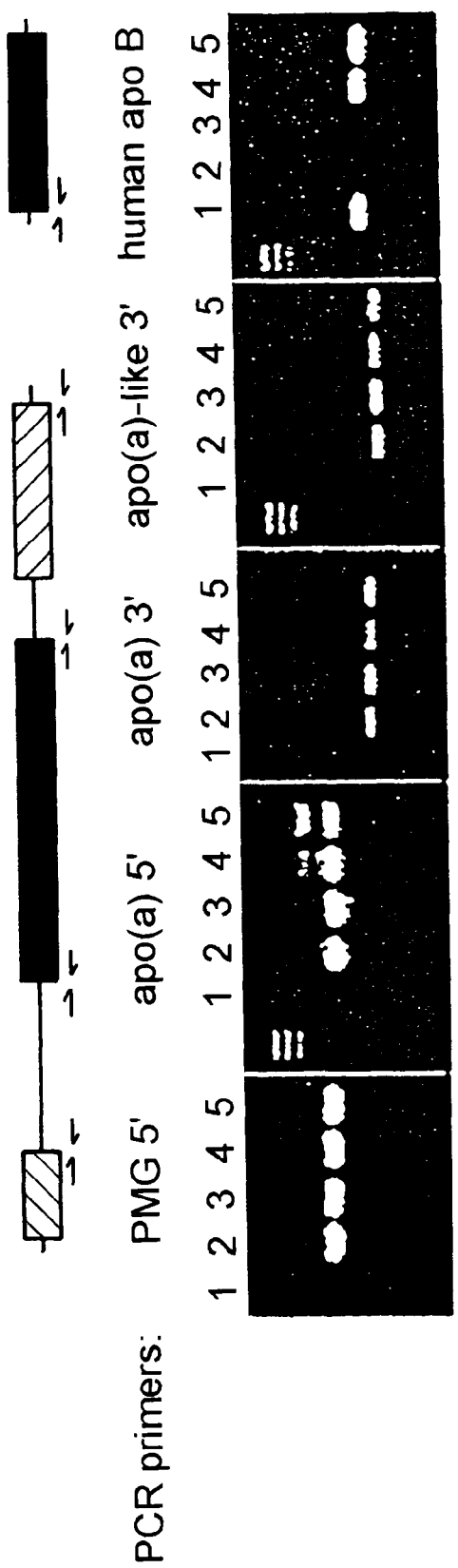
FIG. 1. PCR analysis of human apoB and apo(a) in transgenic rabbits

To create the apo(a) transgenic rabbits, 280 microinjected embryos were transferred into pseudopregnant females, resulting in 17 live-born rabbits. Rabbit DNA, extracted from ear biopsies, was screened for the presence of human apo(a) by PCR using methods and primers described previously (Frazer, et al., *Nat Gen* (1995) 9, 424–431). Two female rabbits were transgenic, and the animal with the highest apo(a) plasma level was used in subsequent studies. PCR screening was used to identify rabbits containing the transgenes and to confirm the complete integration of the apo(a) gene and its flanking regions (FIG. 1). The apo(a) founder rabbits contained an intact copy of the entire YAC genomic clone, as determined by four different PCR reactions spanning the entire length of the clone. To create the apoB transgenics, 780 microinjected embryos were transferred into pseudopregnant females. of the 20 live-born rabbits, two apoB transgenics were identified using ear biopsy DNA, PCR and human apoB specific primers from the promoter region of the gene: 5'-AGAAGGTTCCAGATGTCTATGAGG (SEQ ID No:1) and 5'-TCCAAGTATCTGTCTTCAAGAAACC (SEQ ID NO:2). The animal with the highest apoB plasma level was used in subsequent studies. The human apoB gene was detected by a single PCR reaction specific for human sequences in the promoter region. Offspring of the apo(a) and apoB founder animals were positive for the appropriate markers and demonstrated a Mendelian pattern of transmission of the two transgenes. Mating between the apo(a) and apoB transgenic founders produced rabbits of the predicted genotypes which are the subject of this invention.

Example 3

Analysis of Transgenic apo(a) and ano(b) Tissue Distribution by RT-PCR

Total RNA was extracted from control and transgenic rabbit tissues using RNAstat-60 (Tel-Test B, Frienswood, Tex.), subjected to DNAse treatment, then reverse transcribed [5 µg RNA incubated with 10 ng apo(a)RT primer: 5' -GATGACCAAGCTTGGCAGGTTCTTCC-3' (SEQ ID NO:3), or apoB M46 primer: 5'-CCACATTTTGAATCCAGGATGCAGTACTACT-3' (SEQ ID NO:4) in a volume of 12 µl at 65° C. for 10 minutes, then supplemented with Superscript II/buffer (GibcoBRL, Bethesda, Md.) and incubated for 1 hour at 42° C.]. The first strand cDNA was then treated with RNAse, and extracted with phenol/chloroform. 5 µl of the RT product was subjected to PCR under standard conditions for Taq polymerase (Boehringer Manheim, Indianapolis, Ind.) using 50 pmoles of each primer and thermocycling as follows: (94° C. for 30 seconds, 62° C. for 30 seconds, followed by 72° C. for 90 seconds—25 cycles). Apo(a) cDNA was detected using primers (a)Kr1F: 5' -ACCTGAGCAAAGCCATGTG-3' (SEQ ID NO:5) and (a)Kr1R: 5' -AGTACTCCCACCTGACACCG-3' (SEQ ID NO:6). ApoB cDNA was detected using human and rabbit specific PCR primers (M49/M50human or M49/M50rabbit, Hughes, S. D. et al., *Hum. Gene Ther.*, 7, 39–49 (1996)). PCR products were analyzed on 1.5% agarose gels. To demonstrate the absence of genomic DNA contamination, RNA preparations were directly subjected to the same PCR conditions, and no product was amplified.

To determine the distribution of apo(a) and apoB transgene expression, RNA preparations from several tissues (liver, testes, small intestine, kidney, brain, and lung) were subjected to RT-PCR assays as a qualitative determination of transgene expression (FIG. 2). Apo(a) RNA was detected in the liver and the testes, while under more sensitive conditions (increased number of PCR cycles from 25 to 30), it was also observed in the brain. The liver and testes were also the major sites of expression for the human apoB transgene. A relatively weak signal (<5% of signal in liver) was detected in the small intestine. As a control for the species specificity of the apoB mRNA assay, as well as for RNA quality, the RT-PCR assay was used to detect specifically rabbit apoB. As expected, rabbit apoB mRNA was detected in all tissues examined. Consistent with studies in transgenic mice, both human apo(a) and apoB transgenes were expressed at significant levels and in the appropriate tissues in all founder rabbits identified, demonstrating the high efficiency and tissue specific expression of these genomic transgenes as compared to cDNA transgenes (Chiesa, et al., *J Biol Chem* (1992) 267, 24369–24374; Chiesa, et al., *J Bio Chem* (1993) 268, 23747–23750).

The tissue distribution of human apoB expression was somewhat different to that observed in transgenic mice. The low level human apoB intestinal expression in the transgenic rabbits indicates some basal level of transcription from the human apoB promoter occurs in rabbit intestine, but the expression is far below that of endogenous apoB in the intestine, suggesting that control elements required for expression in this tissue were not present in the apoB genomic construct. This later point is consistent with the conclusions of two independent reports of mice containing an identical apoB transgene (Callow, et al., *Proc Nat'l Acad Sci, USA* (1994) 91, 2130–2136; Purcell-Huynh, et al., *J Clin Invest* (1995) 95, 2246–2257). In addition, we did not detect human apoB-48 in the plasma of transgenic rabbits. This result, consistent with findings of (Fan, et al., Arterioscler Thromb Vasc Biol (1995) 15, 1889–1899) suggests that little or no human apoB protein production occurs in the intestine of the transgenic rabbits.

Because of the profound decrease in apo(a) plasma levels associated with sexual maturity previously noted in mice containing the apo(a) genomic transgene, we examined the effect of sexual maturity on apo(a) plasma levels in the transgenic rabbits. Plasma samples collected from rabbits at 3, 6, and 9 months of age (rabbits are sexually mature at 6 months of age) were evaluated for changes in apo(a) levels by immunoblotting (FIG. 3). This analysis revealed no significant change in apo(a) levels over the course of sexual maturation in the transgenic rabbits.

While the tissue specificity of apo(a) genomic transgene expression was similar in rabbits and mice, developmental regulation of expression differed significantly between these two organisms. Unlike the striking effects of sexual maturity on apo(a) plasma levels in transgenic mice, apo(a) levels in rabbits were not altered by sexual maturation. Since plasma levels of apo(a) are primarily determined by synthetic rate, lack of a decline in apo(a) plasma levels accompanying sexual maturity in rabbits containing the apo(a) transgene suggests that sex hormones do not have a potent effect on transgene expression in these animals. Effects of these hormones on apo(a) transcription in rabbits may be more subtle, as has been noted in humans.

Example 4

Apolipoprotein and Lipoprotein Analysis

The total lipoprotein fraction (r<1.21 g/ml) was prepared from rabbit plasma samples by a density gradient ultracentrifugation method described previously (Callow, et al., *Proc Nat'l Acad Sci, USA* (1994) 91, 2130–2136). Lp(a) and human apoB concentrations were measured in rabbit plasma and lipoprotein fractions by a sandwich ELISA assay. For Lp(a), purified IgG prepared from goat polyclonal antiserum to human apolipoprotein (a) (International Immunology Corp., Murrieta, Calif.) was bound to the microtiter plate well as a capture antibody. A horseradish peroxidase conjugate of the same antibody was used for detection of apo(a) after addition of the chromogenic substrate o-Phenylene diamine. Standardization of the method was based on in-house human lipoprotein calibrators independently measured using a commercially available standardized Lp(a) ELISA kit (Strategic Diagnostics, Newark, Del.). The assay for human apoB (B48+B100) employed a mouse anti-human apoB antibody (Genzyme, Cambridge, Mass.). Standard curves were calculated with appropriate blanks and controls using Logit-Log data transformation. All reported concentrations were calculated from triplicate analysis.

To assess apo(a) and apoB interactions, plasma isolated from the transgenic rabbits was separated by SDS-PAGE on 4% polyacrylamide gels according to (Laemmli, E. K., *Nature* (1970) 227, 680–685) and proteins were transferred to a Millipore nitrocellulose membrane by immunoblotting according to (Towbin, et al., J., *Proc Nat Acad Sci, USA* (1979) 6, 4350–4354). Where indicated, samples were reduced by the addition of denaturing sample buffer containing 2.5% 2-mercaptoethanol and incubated at 100° C. for 5 minutes. Apo(a) was detected with goat anti-apo(a) (Valbiotech, Paris) followed by HRP-conjugated rabbit anti-goat (BioRad, Hercules, Calif.). Human apoB was detected using HRP-conjugated polyclonal rabbit anti-human apoB (kindly provided by C. Fievet). Protein bands were revealed by an enhanced chemiluminescence kit (Amersham, Arlington Heights, IL) and scanned using a Hoefer GS transmittance scanning densitometer. The area of the main peaks were used to evaluate the relative proportion of free and apoB-bound apo(a) (Gabel, et al., *Arterio. Thromb. Vasc. Biol.* (1996) 16, 1559–1567). The apparent molecular weights were determined by the use of prestained standards (BioRad). Control human serum was used as positive control for expression of the human proteins.

Under non-reducing conditions, plasma samples from both the apo(a) transgenic rabbits and the combined human apoB/apo(a) transgenic rabbits demonstrated two bands (FIG. 4A); the higher molecular weight band corresponding to the apoB/apo(a) complex, and the lower molecular weight band corresponding to free apo(a). The presence of a high molecular weight apo(a) band indicated assembly of Lp(a) in the combined transgenic rabbits, as well as some degree of covalent interaction between apo(a) and rabbit apoB in rabbits transgenic for apo(a) only. This result was confirmed by immunoblotting reduced plasma samples (FIG. 4B), where only a single band representing apo(a) was detected in both types of transgenic rabbits using the same human apo(a) antiserum. The apparent molecular weight of the apo(a) in the transgenic rabbits was approximately 200 kD. This is similar to the apo(a) size observed in the transgenic mice containing this same apo(a) genomic construct, corresponding to an apo(a) protein containing approximately nine kringle 4—like repeats. Samples blotted with human specific apoB antiserum (FIG. 4C) gave a single band of 550 kD, representing human apoB-100, exclusively in the plasma of rabbits which tested positive by PCR for human apoB. Concentrations of apo(a) and apoB in the transgenic rabbits were evaluated by ELISA. The average concentration of human apoB in the transgenic rabbits was 17.6 mg/dl. The average total apo(a) concentration in plasma was 2.5 mg/dl, with no significant difference between the apo(a) only and human apoB/apo(a) transgenics.

Ultracentrifugation was used to examine the association of apo(a) with the lipoprotein fraction. The disulfide linkage between apo(a) and human apoB has been shown to withstand the conditions of ultracentrifugation used to isolate lipoproteins, while non-covalently associated apo(a) fractionates with the more dense plasma proteins (Utermann, G., & Weber, W., *FEBS Let* (1983) 154, 357–361). Lipoprotein fractions isolated from apo(a) transgenics and apoB/apo(a) transgenic rabbits were tested for the presence of apo(a) by ELISA. Apo(a) was detected in the lipoprotein fractions of both types of transgenic rabbits, indicating apo(a) formed a disulfide bond between both human and rabbit apoB. The relative proportions of Lp(a) and apo(a) in the plasma, however, suggested that the rabbit apoB-apo(a) complex was formed in vivo at a relatively lower efficiency than that observed with human apoB. Comparing the patterns of apo(a) immunoreactivity between apo(a) transgenic and apoB/apo(a) transgenic rabbits (FIG. 4A) revealed a greater proportion of non-covalently bound apo(a) when only rabbit apoB was present. The relative ratios of the different molecular forms of apo(a) in the transgenic rabbits were estimated from immunoblots by densitometric scanning of chemiluminescent films. In apoB/apo(a) transgenics, approximately 20% of the apo(a) consistently migrated as free apo(a) (n=3), with the remaining 80% covalently bound to either human or rabbit apoB. In apo(a) transgenic rabbits, the reverse distribution was observed (80% free protein and 20% bound to rabbit apoB; n=3). Although these ratios are not rigorously quantitative, the consistent differences between the two groups of transgenic rabbits containing the same apo(a) transgene and similar total apo(a) levels suggest that apo(a) forms a disulfide linkage more efficiently with human apoB than rabbit apoB.

The ability of rabbit apoB to form a covalent linkage with apo(a) was first suggested by in vitro studies examining human apo(a) interactions with apoB from a number of mammals which demonstrated that rabbit apoB may form a covalent interaction with human apo(a) under certain conditions (Trieu, V., & McConathy, W. J., *Biochem. J.* (1995) 309, 899–904). The demonstration of Lp(a) assembly in the rabbits expressing only the apo(a) transgene substantiates this interaction under in vivo conditions. In comparison, rabbits containing both human apoB and apo(a) transgenes contained a much higher proportion of apo(a) in the Lp(a) form. However, despite adequate levels of human apoB in the combined apoB/apo(a) transgenic rabbits, approximately 20% of the apo(a) persisted in a non-covalently bound state. This is in contrast to the condition in humans where all the apo(a) is covalently bound to apoB, and the presence of free apo(a) has been observed only in rare cases of abetalipoproteinemia (Menzel, et al., *J Bio Chem* (1990) 265, 981–986).

Example 5

Fractionation of Plasma Lipoproteins and Cholesterol Measurement

Freshly isolated plasma was fractionated by gel permeation chromatography using a Superose 6 column (Pharmacia). 100 µl of plasma was injected onto the column and run under isocratic conditions with a flow rate of 40 µl/min in GF2 buffer (20 mM Tris pH 8.0, 0.27 mM EDTA, 150 mM NaCl). The effluent was monitored for absorbance at 280 nm, and 50 µl fractions were collected during the run and subsequently assayed for cholesterol using a commercial cholesterol assay kit (Boehringer-Mannheim). A 20 µl aliquot of cholesterol-containing fractions was used to detect the presence of apo(a) and Lp(a) using electrophoresis and immunoblotting as described above.

To further characterize the association of apo(a) with lipoproteins in the transgenic rabbits, lipoproteins were size-fractionated by gel filtration chromatography. In contrast to density gradient centrifugation methods, chromatographic methods can isolate lipoprotein complexes containing proteins associated by weak, non-covalent interactions. Immuno-blotting of plasma fractionated in this manner showed that apo(a) was present primarily in the LDL fraction in both human apoB/apo(a) (FIG. 5A) and apo(a) transgenic rabbits (FIG. 5B). LDL fractions of combined transgenic rabbits contained two distinct high molecular weight bands corresponding to the human apoB/apo(a) complex and rabbit apoB/apo(a) complex, distinguished on the basis of the lower molecular weight of rabbit apoB-100 (320 kD). Non-covalently associated apo(a), although present in the immunoblot of total plasma, was not detected in the LDL fractions of human apoB/apo(a) transgenic rabbits. LDL fractions of apo(a) transgenic rabbits contained a broad band representing rabbit apoB/apo(a) complex accompanied by a relatively larger amount of apo(a) dissociated from LDL under electrophoresis conditions, designated as free apo(a) (FIG. 5B). This analysis confirmed the association of apo(a) with lipoproteins containing both human and rabbit apoB, although in the case of rabbit apoB, apo(a) was linked through a disulfide bond in a much lower proportion of particles.

In the present invention, apo(a) exhibited specific non-covalent interactions with apoB-containing lipoproteins, suggesting a highly conserved affinity between apo(a) and apoB, similar to results of previous studies of apo(a) interactions with apoB of several other species (Chiesa, et al., *J Bio Chem* (1993) 268, 23747–23750; Trieu, V., & McConathy, W. J., *Biochem. J.* (1995) 309, 899–904). This is supported by the observation of non-covalently associated apo(a) in the LDL fraction of apo(a) transgenic rabbits. Such non-covalent interactions between apo(a) and apoB have been proposed to facilitate Lp(a) assembly by bringing cysteine residues in position for disulfide bond formation (Trieu, V., & McConathy, W. J., *J. Biol. Chem.* (1995) 270, 15471–15474). In the plasma of the apoB/apo(a) transgenic rabbits, apo(a) may persist in this non-covalently bound form due to the capacity of rabbit apoB to effectively trap some apo(a) in the initial binding step, while disulfide bond formation from this intermediate procedes with much lower efficiency since covalent linkage must occur between cysteines which are not optimally positioned through non-covalent interactions.

Example 6

Sequence Comparison of Putative apo(a) Binding Site in Human and Rabbit apoB Due to the surprising ability of rabbit apoB, unlike murine apoB, to form a covalent linkage with human apo(a), we made a comparison of its amino acid sequence within a region homologous to the site of apo(a) attachment in human apoB. Since the relevant portion of rabbit apoB has not been reported, the carboxy-terminal region of a rabbit apoB cDNA clone was sequenced. The derived protein sequence for rabbit apoB is shown in FIG. 6 aligned within a region of significant homology to four other reported apoB sequences, including human (SEQ ID NOS:7–11). As in rodents and pigs, two mammals in which apoB has been demonstrated unable to form a covalent linkage with human apo(a) in vitro, rabbit apoB also lacks a cysteine at a position homologous to the site of apo(a) attachment in human apoB (cys4326). These results, in contrast to two previous reports suggesting that a cysteine residue at this position is required for covalent interaction with apo(a) (Callow, M. J., & Rubin, E. M., *J Biol Chem* (1995) 270, 23914–23917; McCormick, S. P. A., Ng, J. K., Taylor, S., Flynn, L. M., Hammer, R. E., & Young, S. G., (1995) 92, 10147–10151), indicate that cysteines elsewhere in the rabbit apoB molecule are capable of covalent interaction with apo(a).

All the references discussed herein are incorporated by reference.

One skilled in the art will readily appreciate the present invention is well adapted to carry out the objects and obtain the ends and advantages mentioned, as well as those inherent therein. The transgenic animals, methods, procedures and techniques described herein are presented as representative of the preferred embodiments, and intended to be exemplary and not intended as limitations on the scope of the present invention. Changes therein and other uses will occur to those of skill in the art which are encompassed within the spirit of the invention or defined by the scope of the appended claims.

We claim:

1. A transgenic rabbit whose genome comprises a first nucleic acid sequence, which encodes a human apolipoprotein (a) polypeptide, and a second nucleic acid sequence, which encodes a human apolipoprotein B polypeptide, said first and second nucleic acid sequences being operatively associated with a first and second promoter region, respectively, for functional transcription such that said human apolipoprotein (a) and human apolipoprotein B polypeptides are expressed in such a manner that they combine in vivo in said transgenic rabbit to produce human lipoprotein (a).

2. The rabbit of claim 1 wherein said rabbit develops human-like atherosclerotic lesions when fed a cholesterol rich diet.

3. The rabbit of claim 1 wherein the first and second nucleic acid sequences are selected from the group consisting of genomic DNA and cDNA.

4. The rabbit of claim 1 having liver cells which express said sequences.

5. The rabbit of claim 1 having testes cells which express said sequences.

6. The rabbit of claim 1 having a stable plasma level of human apolipoprotein (a) polypeptide throughout its sexual maturity.

7. The transgenic rabbit according to claim 1 wherein said first and second promoter regions are human promoters.

8. The transgenic rabbit according to claim 1 wherein said first and second promoter regions are selected, individually, from the group consisting of: promoter sequences derived from a rabbit cell; viral promoter sequences; apoAI promoters; hepatic enhancers of apoE; intestinal enhancers of apoCIII; ubiquitous promoters; filament promoters; MDR, CFTR and factor promoters; tissue-specific promoters; promoters which are preferentially activated in dividing cells; promoters which respond to a stimulus; tetracycline-regulated transcriptional modulators; and metallothionein promoters.

9. A process for making a transgenic rabbit which is capable of producing human lipoprotein (a) comprising mating a first rabbit which has a genome comprising a first nucleic acid sequence encoding a human apolipoprotein (a) polypeptide and is capable of expressing human apolipoprotein (a) with a second rabbit which has a genome comprising a second nucleic acid sequence encoding a human apolipoprotein B polypeptide and is capable of expressing human apolipoprotein B, said first and second nucleic acid sequences being operatively associated with a first and second promoter region, respectively, for functional transcription such that said human apolipoprotein (a) and human apolipoprotein B polypeptides are expressed in such a manner that they combine in vivo in said transgenic rabbit to produce human lipoprotein (a).

10. The process of claim 9 wherein said rabbit capable of expressing human apolipoprotein B protein is provided by injecting a rabbit embryo with a phagemid which contains the human apolipoprotein B gene.

11. The process of claim 9 wherein said rabbit capable of expressing human apolipoprotein (a) is provided by injecting a rabbit embryo with a yeast artificial chromosome which contains a human apolipoprotein (a) gene.

12. The process of claim 9 wherein said rabbit expressing human apolipoprotein (a) is provided by infecting a rabbit blastomere with a retrovirus comprising at least one human DNA fragment encoding apolipoprotein (a) protein and transferring the blastomere to a recipient female rabbit.

13. The process of claim 9 wherein said rabbit expressing human apolipoprotein B is provided by infecting a rabbit blastomere with a retrovirus comprising at least one human DNA fragment encoding apolipoprotein B protein, and transferring the blastomere to a recipient female rabbit.

14. A method for determining whether a compound can treat atherosclerosis or an undesirable lipid profile comprising:

comparing the lipid profile or state of atherosclerosis in a first transgenic rabbit fed a cholesterol-rich diet and treated with said compound, to the lipid profile or state of atherosclerosis in a second transgenic rabbit fed a cholesterol-rich diet but not treated with said compound; and determining the potential therapeutic effect of said compound based upon comparative evaluation of the lipid profile or state of atherosclerosis in said first and second transgenic rabbits;

wherein said first and second transgenic rabbits are capable of producing human lipoprotein (a), develop human-like atherosclerotic lesions when fed a cholesterol-rich diet, and have within their genomic DNA sequences which encode human apolipoprotein (a) and human apolipoprotein B polypeptides, said sequences being operatively associated with a first and second promoter region, respectively, such that said human apolipoprotein (a) and human apolipoprotein B polypeptides are expressed in such a mamer that they combine in vivo in said transgenic rabbits to produce human lipoprotein (a).

15. A method for determining whether a compound can inhibit assembly of a human lipoprotein (a) particle comprising comparing the level of human lipoprotein (a) production in a first transgenic rabbit which has been treated with said compound and which is capable of producing human lipoprotein (a) to the level of production of human lipoprotein (a) in a second transgenic rabbit that has not been treated with said compound and which is capable of producing human lipoprotein (a), said first and second transgenic rabbits each having within their genomic DNA sequences which encode human apolipoprotein (a) and human apolipoprotein B polypeptides, said sequences being operatively associated with a first and second promoter region, respectively, such that said human apolipoprotein (a) and human apolipoprotein B polypeptides are expressed in such a manner that they combine in vivo in said transgenic rabbits to produce human lipoprotein (a).

16. The method of claim 15 wherein said compound is selected from the group consisting of an antisense nucleic acid and an intracellular binding protein.

17. A transgenic rabbit whose genome comprises a first nucleic acid sequence, which encodes a human apolipoprotein (a) polypeptide, and a second nucleic acid sequence, which encodes a human apolipoprotein B polypeptide, said first and second nucleic acid sequences being operatively associated with a first and second promoter region, respectively, for functional transcription such that apolipoprotein (a) polypeptide plasma level is stable throughout the sexual maturity of said rabbit and about 80% of said apolipoprotein (a) polypeptide is covalently bound to human apolipoprotein B or rabbit apolipoprotein B.

18. A transgenic rabbit whose genome comprises a first nucleic acid sequence, which encodes a human apolipoprotein (a) polypeptide, and a second nucleic acid sequence, which encodes a human apolipoprotein B polypeptide, said first and second nucleic acid sequences being operatively associated with their respective natural promoter regions for functional transcription such that said human apolipoprotein (a) and human apolipoprotein B polypeptides combine in vivo in said transgenic rabbit to produce human lipoprotein (a).

19. The rabbit of claim 18, wherein said rabbit has a stable plasma level of human apolipoprotein (a) polypeptide throughout its sexual maturity and about 80% of said human apolipoprotein (a) polypeptide is covalently bound to human apolipoprotein B or rabbit apolipoprotein B.

20. A method for determining whether a compound can treat atherosclerosis or an undesirable lipid profile comprising:
   comparing the lipid profile or state of atherosclerosis in a first transgenic rabbit fed a cholesterol-rich diet and treated with said compound, to the lipid profile or state of atherosclerosis in a second transgenic rabbit fed a cholesterol-rich diet but not treated with said compound; and
   determining the potential therapeutic effect of said compound based upon comparative evaluation of the lipid profile or state of atherosclerosis in said first and second transgenic rabbit;
   wherein said first and second transgenic rabbits each being a transgenic rabbit of claim 18.

21. A method for determining whether a compound can inhibit assembly of a human lipoprotein (a) particle comprising comparing the level of human lipoprotein (a) production in a first transgenic rabbit which has been treated with said compound and which is capable of producing human lipoprotein (a) to the level of production of human lipoprotein (a) in a second transgenic rabbit that has not been treated with said compound and which is capable of producing human lipoprotein (a), said first and second transgenic rabbits each being a transgenic rabbit of claim 18.

22. A process for making a transgenic rabbit which is capable of producing human lipoprotein (a) comprising mating a first rabbit which has a genome comprising a first nucleic acid sequence encoding a human apolipoprotein (a) polypeptide and is capable of expressing human apolipoprotein (a) with a second rabbit which has a genome comprising a second nucleic acid sequence encoding a human apolipoprotein B polypeptide and is capable of expressing human apolipoprotein B, said first and second nucleic acid sequences being operatively associated with their respective natural promoter regions for functional transcription such that said human apolipoprotein (a) and human apolipoprotein B polypeptides combine in vivo in said transgenic rabbit to produce human lipoprotein (a).

* * * * *

SEQUENCE LISTING

<160> NUMBER OF SEQ ID NOS: 11

<210> SEQ ID NO 1
<211> LENGTH: 24
<212> TYPE: DNA
<213> ORGANISM: Homo sapiens

<400> SEQUENCE: 1
agaaggttcc agatgtctat gagg                24

<210> SEQ ID NO 2
<211> LENGTH: 25
<212> TYPE: DNA
<213> ORGANISM: Homo sapiens

<400> SEQUENCE: 2
tccaagtatc tgtcttcaag aaacc               25

<210> SEQ ID NO 3
<211> LENGTH: 26
<212> TYPE: DNA
<213> ORGANISM: Homo sapiens

<400> SEQUENCE: 3
gatgaccaag cttggcaggt tcttcc              26

<210> SEQ ID NO 4
<211> LENGTH: 31
<212> TYPE: DNA
<213> ORGANISM: Homo sapiens

<400> SEQUENCE: 4
ccacattttg aatccaggat gcagtactac t         31

<210> SEQ ID NO 5
<211> LENGTH: 19
<212> TYPE: DNA
<213> ORGANISM: Homo sapiens

<400> SEQUENCE: 5
acctgagcaa agccatgtg                      19

<210> SEQ ID NO 6
<211> LENGTH: 20
<212> TYPE: DNA
<213> ORGANISM: Homo sapiens

<400> SEQUENCE: 6
agtactccca cctgacaccg                     20

<210> SEQ ID NO 7
<211> LENGTH: 50
<212> TYPE: PRT
<213> ORGANISM: Oryctolagus cuniculus

<400> SEQUENCE: 7

Ala Tyr Ile Val Arg His Met Lys Glu Asn Leu Tyr Phe Asn Leu Gly
 1               5                  10                  15

Lys Phe Asn Glu Phe Val Gln Asn Lys Leu Lys Ala Ala Ser Gln Glu
            20                  25                  30

Leu Gln Gln Ile Gln Gln His Ile Lys Ala Leu Arg Lys Glu Tyr Phe
        35                  40                  45

Asp Pro
    50

<210> SEQ ID NO 8
<211> LENGTH: 50
<212> TYPE: PRT
<213> ORGANISM: Homo sapiens

<400> SEQUENCE: 8

Pro Tyr Val Phe Lys Leu Leu Lys Glu Asn Leu Cys Leu Asn Leu His
 1               5                  10                  15

Lys Phe Asn Glu Phe Ile Gln Asn Glu Leu Gln Glu Ala Ser Gln Glu
            20                  25                  30

Leu Gln Gln Ile His Gln Tyr Ile Met Ala Leu Arg Glu Glu Tyr Phe
        35                  40                  45

Asp Pro
    50

<210> SEQ ID NO 9
<211> LENGTH: 50
<212> TYPE: PRT
<213> ORGANISM: Rattus sp.

<400> SEQUENCE: 9

Pro Phe Ala Phe Lys Ser Leu Arg Glu Asn Ile Tyr Ser Val Phe Ser
 1               5                  10                  15

Glu Phe Asn Asp Phe Val Gln Ser Ile Leu Gln Glu Gly Ser Tyr Lys
            20                  25                  30

Leu Gln Gln Val His Gln Tyr Asn Lys Ala Phe Arg Glu Glu Tyr Phe
        35                  40                  45

Asp Pro
    50

<210> SEQ ID NO 10
<211> LENGTH: 50
<212> TYPE: PRT
<213> ORGANISM: Sus scrofa

<400> SEQUENCE: 10

Pro Leu Gly Phe Arg Leu Leu Lys Glu Asn Leu Asp Ser Pro Phe Gly
 1               5                  10                  15

Met Leu Asn Glu Phe Ile Gln Asn Thr Leu Trp Glu Ala Ser Gln Glu
            20                  25                  30

Leu Gln Gln Leu His Gln Tyr Ile Lys Ala Leu Arg Lys Glu Tyr Phe
        35                  40                  45

Asp Pro
    50

```
<210> SEQ ID NO 11
<211> LENGTH: 50
<212> TYPE: PRT
<213> ORGANISM: Gallus gallus

<400> SEQUENCE: 11

Ala His Lys Leu Arg Ser Leu Ala Glu Asn Val Lys Lys Tyr Ile Ser
 1               5                  10                  15

Gln Ile Lys Asn Phe Ser Gln Lys Thr Leu Gln Lys Leu Ser Glu Asn
            20                  25                  30

Leu Gln Gln Leu Val Leu Tyr Ile Lys Ala Leu Arg Glu Glu Tyr Phe
        35                  40                  45

Asp Pro
    50
```